(12) United States Patent
Krone et al.

(10) Patent No.: US 12,137,910 B2
(45) Date of Patent: *Nov. 12, 2024

(54) TISSUE GRASPING DEVICES AND RELATED METHODS

(71) Applicant: Evalve, Inc., Santa Clara, CA (US)

(72) Inventors: Ryan T. Krone, San Francisco, CA (US); Jacob L. Greenberg, Redwood City, CA (US); Raghuveer Basude, Fremont, CA (US)

(73) Assignee: Evalve, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/363,814

(22) Filed: Aug. 2, 2023

(65) Prior Publication Data

US 2023/0371952 A1 Nov. 23, 2023

Related U.S. Application Data

(63) Continuation of application No. 17/384,233, filed on Jul. 23, 2021, now Pat. No. 11,759,209, which is a
(Continued)

(51) Int. Cl.
*A61B 17/08* (2006.01)
*A61B 17/00* (2006.01)

(52) U.S. Cl.
CPC ........ *A61B 17/08* (2013.01); *A61B 17/00234* (2013.01); *A61B 2017/00243* (2013.01);
(Continued)

(58) Field of Classification Search
CPC .......... A61F 2/24; A61F 2/2427; A61F 2/246; A61F 2/2463; A61F 2/2466;
(Continued)

(56) References Cited

U.S. PATENT DOCUMENTS 2,097,018 A 10/1937 Chamberlin
2,108,206 A 2/1938 Meeker
(Continued)

FOREIGN PATENT DOCUMENTS

AU 2002316473 12/2008
CN 1262244 7/2006
(Continued)

OTHER PUBLICATIONS

U.S. Appl. No. 14/677,294, dated Aug. 23, 2017 Response to Restriction Requirement.
(Continued)

*Primary Examiner* — Ryan J. Severson
(74) *Attorney, Agent, or Firm* — SLEMAN & LUND LLP

(57) ABSTRACT

A tissue gripping device is formed from a shape-memory material, and has a base section, a first arm, and a second arm disposed opposite the first arm, each arm having a first end coupled to the base section and a free end extending from the base section. The arms of the tissue gripping device are configured to resiliently flex toward a relaxed configuration in a distal direction as the tissue gripping device is moved from a pre-deployed configuration toward a deployed configuration. The tissue gripping device is usable in a method for gripping tissue. The method includes positioning the tissue gripping device near target tissue and moving the tissue gripping device from a pre-deployed configuration toward a deployed configuration in order to grip the target tissue.

20 Claims, 11 Drawing Sheets

Related U.S. Application Data continuation of application No. 16/883,382, filed on May 26, 2020, now Pat. No. 11,096,691, which is a continuation of application No. 14/805,275, filed on Jul. 21, 2015, now Pat. No. 10,667,815.

(52) U.S. Cl.
CPC ............... *A61B 2017/00526* (2013.01); *A61B 2017/00783* (2013.01); *A61B 2017/00867* (2013.01)

(58) Field of Classification Search
CPC ........... A61B 2017/00243; A61B 2017/00526; A61B 2017/00783; A61B 2017/00867; A61B 2017/081; A61B 17/00234; A61B 17/08

See application file for complete search history.

(56) References Cited

U.S. PATENT DOCUMENTS

| | | |
|---|---|---|
| 3,296,668 A | 1/1967 | Aiken |
| 3,378,010 A | 4/1968 | Codling |
| 3,557,780 A | 1/1971 | Sato |
| 3,671,979 A | 6/1972 | Moulopoulos |
| 3,675,639 A | 7/1972 | Cimber |
| 3,874,338 A | 4/1975 | Happel |
| 3,874,388 A | 4/1975 | King |
| 4,007,743 A | 2/1977 | Blake |
| 4,056,854 A | 11/1977 | Boretos |
| 4,064,881 A | 12/1977 | Meredith |
| 4,091,815 A | 5/1978 | Larsen |
| 4,112,951 A | 9/1978 | Hulka |
| 4,235,238 A | 11/1980 | Ogiu |
| 4,297,749 A | 11/1981 | Davis |
| 4,425,908 A | 1/1984 | Simon |
| 4,458,682 A | 7/1984 | Cerwin |
| 4,484,579 A | 11/1984 | Meno |
| 4,487,205 A | 12/1984 | Di Giovanni |
| 4,498,476 A | 2/1985 | Cerwin |
| 4,510,934 A | 4/1985 | Batra |
| 4,531,522 A | 7/1985 | Bedi |
| 4,578,061 A | 3/1986 | Lemelson |
| 4,641,366 A | 2/1987 | Yokoyama |
| 4,686,965 A | 8/1987 | Bonnet |
| 4,777,951 A | 10/1988 | Cribier |
| 4,809,695 A | 3/1989 | Gwathmey |
| 4,917,089 A | 4/1990 | Sideris |
| 4,944,295 A | 7/1990 | Gwathmey |
| 4,969,890 A | 11/1990 | Sugita |
| 4,994,077 A | 2/1991 | Dobben |
| 5,015,249 A | 5/1991 | Nakao |
| 5,019,096 A | 5/1991 | Fox, Jr. |
| 5,042,707 A | 8/1991 | Taheri |
| 5,047,041 A | 9/1991 | Samuels |
| 5,049,153 A | 9/1991 | Nakao |
| 5,061,277 A | 10/1991 | Carpentier |
| 5,069,679 A | 12/1991 | Taheri |
| 5,108,368 A | 4/1992 | Hammerslag |
| 5,125,758 A | 6/1992 | Dewan |
| 5,171,252 A | 12/1992 | Friedland |
| 5,171,259 A | 12/1992 | Inoue |
| 5,190,554 A | 3/1993 | Coddington, III |
| 5,195,968 A | 3/1993 | Lundquist |
| 5,209,756 A | 5/1993 | Seedhom |
| 5,226,429 A | 7/1993 | Kuzmak |
| 5,226,911 A | 7/1993 | Chee |
| 5,234,437 A | 8/1993 | Sepetka |
| 5,242,456 A | 9/1993 | Nash |
| 5,250,071 A | 10/1993 | Palermo |
| 5,251,611 A | 10/1993 | Zehel |
| 5,254,130 A | 10/1993 | Poncet |
| 5,261,916 A | 11/1993 | Engelson |
| 5,271,381 A | 12/1993 | Ailinger |
| 5,275,578 A | 1/1994 | Adams |
| 5,282,845 A | 2/1994 | Bush |
| 5,304,131 A | 4/1994 | Paskar |
| 5,306,283 A | 4/1994 | Conners |
| 5,306,286 A | 4/1994 | Stack |
| 5,312,415 A | 5/1994 | Palermo |
| 5,314,424 A | 5/1994 | Nicholas |
| 5,318,525 A | 6/1994 | West |
| 5,320,632 A | 6/1994 | Heidmueller |
| 5,325,845 A | 7/1994 | Adair |
| 5,330,442 A | 7/1994 | Green |
| 5,332,402 A | 7/1994 | Teitelbaum |
| 5,342,393 A | 8/1994 | Stack |
| 5,350,397 A | 9/1994 | Palermo |
| 5,350,399 A | 9/1994 | Erlebacher |
| 5,359,994 A | 11/1994 | Krauter |
| 5,368,564 A | 11/1994 | Savage |
| 5,368,601 A | 11/1994 | Sauer |
| 5,383,886 A | 1/1995 | Kensey |
| 5,391,182 A | 2/1995 | Chin |
| 5,403,312 A | 4/1995 | Yates |
| 5,403,326 A | 4/1995 | Harrison |
| 5,411,552 A | 5/1995 | Andersen |
| 5,417,699 A | 5/1995 | Klein |
| 5,417,700 A | 5/1995 | Egan |
| 5,423,857 A | 6/1995 | Rosenman |
| 5,423,858 A | 6/1995 | Bolanos |
| 5,423,882 A | 6/1995 | Jackman |
| 5,431,666 A | 7/1995 | Sauer |
| 5,437,551 A | 8/1995 | Chalifoux |
| 5,437,681 A | 8/1995 | Meade |
| 5,447,966 A | 9/1995 | Hermes |
| 5,450,860 A | 9/1995 | O'Connor |
| 5,456,400 A | 10/1995 | Shichman |
| 5,456,684 A | 10/1995 | Schmidt |
| 5,462,527 A | 10/1995 | Stevens-Wright |
| 5,472,044 A | 12/1995 | Hall |
| 5,476,470 A | 12/1995 | Fitzgibbons, Jr. |
| 5,477,856 A | 12/1995 | Lundquist |
| 5,478,309 A | 12/1995 | Sweezer |
| 5,478,353 A | 12/1995 | Yoon |
| 5,487,746 A | 1/1996 | Yu |
| 5,496,332 A | 3/1996 | Sierra |
| 5,507,725 A | 4/1996 | Savage |
| 5,507,755 A | 4/1996 | Gresl |
| 5,507,757 A | 4/1996 | Sauer |
| 5,520,701 A | 5/1996 | Lerch |
| 5,522,873 A | 6/1996 | Jackman |
| 5,527,313 A | 6/1996 | Scott |
| 5,527,321 A | 6/1996 | Hinchliffe |
| 5,527,322 A | 6/1996 | Klein |
| 5,536,251 A | 7/1996 | Evard |
| 5,540,705 A | 7/1996 | Meade |
| 5,542,949 A | 8/1996 | Yoon |
| 5,554,185 A | 9/1996 | Block |
| 5,562,678 A | 10/1996 | Booker |
| 5,569,274 A | 10/1996 | Rapacki |
| 5,571,085 A | 11/1996 | Accisano, III |
| 5,571,137 A | 11/1996 | Marlow |
| 5,571,215 A | 11/1996 | Sterman |
| 5,575,802 A | 11/1996 | McQuilkin |
| 5,582,611 A | 12/1996 | Tsuruta |
| 5,593,424 A | 1/1997 | Northrup, III |
| 5,593,435 A | 1/1997 | Carpentier |
| 5,609,598 A | 3/1997 | Laufer |
| 5,618,306 A | 4/1997 | Roth et al. |
| 5,620,452 A | 4/1997 | Yoon |
| 5,620,461 A | 4/1997 | Muijs Van De Moer |
| 5,626,588 A | 5/1997 | Sauer |
| 5,634,932 A | 6/1997 | Schmidt |
| 5,636,634 A | 6/1997 | Kordis |
| 5,639,277 A | 6/1997 | Mariant |
| 5,640,955 A | 6/1997 | Ockuly |
| 5,649,937 A | 7/1997 | Bito |
| 5,662,681 A | 9/1997 | Nash |
| 5,669,917 A | 9/1997 | Sauer |
| 5,690,671 A | 11/1997 | McGurk |
| 5,695,504 A | 12/1997 | Gifford, III |
| 5,695,505 A | 12/1997 | Yoon |
| 5,702,825 A | 12/1997 | Keita |
| 5,706,824 A | 1/1998 | Whittier |

(56) References Cited

U.S. PATENT DOCUMENTS

| | | |
|---|---|---|
| 5,709,707 A | 1/1998 | Lock |
| 5,713,910 A | 2/1998 | Gordon |
| 5,713,911 A | 2/1998 | Racenet |
| 5,715,817 A | 2/1998 | Stevens-Wright |
| 5,716,367 A | 2/1998 | Koike |
| 5,718,725 A | 2/1998 | Sterman |
| 5,719,725 A | 2/1998 | Nakao |
| 5,722,421 A | 3/1998 | Francese |
| 5,725,542 A | 3/1998 | Yoon |
| 5,725,556 A | 3/1998 | Moser |
| 5,738,649 A | 4/1998 | MacOviak |
| 5,741,280 A | 4/1998 | Fleenor |
| 5,749,828 A | 5/1998 | Yeung |
| 5,759,193 A | 6/1998 | Burbank |
| 5,769,812 A | 6/1998 | Stevens |
| 5,769,863 A | 6/1998 | Garrison |
| 5,772,578 A | 6/1998 | Heimberger |
| 5,782,845 A | 7/1998 | Shewchuk |
| 5,797,927 A | 8/1998 | Yoon |
| 5,797,960 A | 8/1998 | Stevens |
| 5,810,847 A | 9/1998 | Laufer |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck |
| 5,823,956 A | 10/1998 | Roth |
| 5,824,065 A | 10/1998 | Gross |
| 5,827,237 A | 10/1998 | Macoviak |
| 5,829,447 A | 11/1998 | Stevens |
| 5,833,671 A | 11/1998 | MacOviak |
| 5,836,955 A | 11/1998 | Buelna |
| 5,840,081 A | 11/1998 | Andersen |
| 5,843,031 A | 12/1998 | Hermann |
| 5,849,019 A | 12/1998 | Yoon |
| 5,853,422 A | 12/1998 | Huebsch |
| 5,855,271 A | 1/1999 | Eubanks |
| 5,855,590 A | 1/1999 | Malecki |
| 5,855,614 A | 1/1999 | Stevens |
| 5,860,990 A | 1/1999 | Nobles |
| 5,861,003 A | 1/1999 | Latson |
| 5,868,733 A | 2/1999 | Ockuly |
| 5,876,399 A | 3/1999 | Chia |
| 5,879,307 A | 3/1999 | Chio |
| 5,885,258 A | 3/1999 | Sachdeva |
| 5,885,271 A | 3/1999 | Hamilton |
| 5,891,160 A | 4/1999 | Williamson, IV |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc |
| 5,954,732 A | 9/1999 | Hart |
| 5,957,949 A | 9/1999 | Leonhardt |
| 5,972,020 A | 10/1999 | Carpentier |
| 5,972,030 A | 10/1999 | Garrison |
| 5,980,455 A | 11/1999 | Daniel |
| 5,989,284 A | 11/1999 | Laufer |
| 6,007,552 A | 12/1999 | Fogarty |
| 6,015,417 A | 1/2000 | Reynolds, Jr. |
| 6,019,722 A | 2/2000 | Spence |
| 6,022,360 A | 2/2000 | Reimels |
| 6,033,378 A | 3/2000 | Lundquist |
| 6,036,699 A | 3/2000 | Andreas |
| 6,048,351 A | 4/2000 | Gordon |
| 6,056,769 A | 5/2000 | Epstein |
| 6,059,757 A | 5/2000 | MacOviak |
| 6,060,628 A | 5/2000 | Aoyama |
| 6,060,629 A | 5/2000 | Pham |
| 6,063,106 A | 5/2000 | Gibson |
| 6,066,146 A | 5/2000 | Carroll |
| 6,068,628 A | 5/2000 | Fanton |
| 6,068,629 A | 5/2000 | Haissaguerre |
| 6,077,214 A | 6/2000 | Mortier |
| 6,086,600 A | 7/2000 | Kortenbach |
| 6,088,889 A | 7/2000 | Luther |
| 6,099,505 A | 8/2000 | Ryan |
| 6,099,553 A | 8/2000 | Hart |
| 6,110,145 A | 8/2000 | MacOviak |
| 6,117,144 A | 9/2000 | Nobles |
| 6,117,159 A | 9/2000 | Huebsch |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt |
| 6,143,024 A | 11/2000 | Campbell |
| 6,159,240 A | 12/2000 | Sparer |
| 6,162,233 A | 12/2000 | Williamson, IV |
| 6,165,164 A | 12/2000 | Hill |
| 6,165,183 A | 12/2000 | Kuehn |
| 6,165,204 A | 12/2000 | Levinson |
| 6,168,614 B1 | 1/2001 | Andersen |
| 6,171,320 B1 | 1/2001 | Monassevitch |
| 6,182,664 B1 | 2/2001 | Cosgrove |
| 6,187,003 B1 | 2/2001 | Buysse |
| 6,190,408 B1 | 2/2001 | Melvin |
| 6,203,531 B1 | 3/2001 | Ockuly |
| 6,203,553 B1 | 3/2001 | Robertson |
| 6,206,893 B1 | 3/2001 | Klein |
| 6,206,907 B1 | 3/2001 | Marino |
| 6,210,419 B1 | 4/2001 | Mayenberger |
| 6,210,432 B1 | 4/2001 | Solem |
| 6,245,079 B1 | 6/2001 | Nobles |
| 6,267,746 B1 | 7/2001 | Bumbalough |
| 6,267,781 B1 | 7/2001 | Tu |
| 6,269,819 B1 | 8/2001 | Oz |
| 6,277,555 B1 | 8/2001 | Duran |
| 6,283,127 B1 | 9/2001 | Sterman |
| 6,283,962 B1 | 9/2001 | Tu |
| 6,299,637 B1 | 10/2001 | Shaolian |
| 6,306,133 B1 | 10/2001 | Tu |
| 6,312,447 B1 | 11/2001 | Grimes |
| 6,319,250 B1 | 11/2001 | Falwell |
| 6,322,559 B1 | 11/2001 | Daulton |
| 6,332,893 B1 | 12/2001 | Mortier |
| 6,352,708 B1 | 3/2002 | Duran |
| 6,355,030 B1 | 3/2002 | Aldrich |
| 6,358,277 B1 | 3/2002 | Duran |
| 6,368,326 B1 | 4/2002 | Dakin |
| 6,387,104 B1 | 5/2002 | Pugsley, Jr. |
| 6,402,780 B2 | 6/2002 | Williamson, IV |
| 6,402,781 B1 | 6/2002 | Langberg |
| 6,406,420 B1 | 6/2002 | McCarthy |
| 6,419,669 B1 | 7/2002 | Frazier |
| 6,447,524 B1 | 9/2002 | Knodel |
| 6,461,366 B1 | 10/2002 | Seguin |
| 6,464,707 B1 | 10/2002 | Bjerken |
| 6,482,224 B1 | 11/2002 | Michler |
| 6,485,489 B2 | 11/2002 | Teirstein |
| 6,508,828 B1 | 1/2003 | Akerfeldt |
| 6,533,796 B1 | 3/2003 | Sauer |
| 6,537,314 B2 | 3/2003 | Langberg |
| 6,540,755 B2 | 4/2003 | Ockuly |
| 6,551,331 B2 | 4/2003 | Nobles |
| 6,562,037 B2 | 5/2003 | Paton |
| 6,562,052 B2 | 5/2003 | Nobles |
| 6,575,971 B2 | 6/2003 | Hauck |
| 6,585,761 B2 | 7/2003 | Taheri |
| 6,599,311 B1 | 7/2003 | Biggs |
| 6,616,684 B1 | 9/2003 | Vidlund |
| 6,619,291 B2 | 9/2003 | Hlavka |
| 6,626,899 B2 | 9/2003 | Houser |
| 6,626,930 B1 | 9/2003 | Allen |
| 6,629,534 B1 | 10/2003 | St Goar |
| 6,641,592 B1 | 11/2003 | Sauer |
| 6,656,221 B2 | 12/2003 | Taylor |
| 6,669,687 B1 | 12/2003 | Saadat |
| 6,685,648 B2 | 2/2004 | Flaherty |
| 6,689,164 B1 | 2/2004 | Seguin |
| 6,695,866 B1 | 2/2004 | Kuehn |
| 6,701,929 B2 | 3/2004 | Hussein |
| 6,702,825 B2 | 3/2004 | Frazier |
| 6,702,826 B2 | 3/2004 | Liddicoat |

(56) References Cited

U.S. PATENT DOCUMENTS

| | | |
|---|---|---|
| 6,709,382 B1 | 3/2004 | Horner |
| 6,709,456 B2 | 3/2004 | Langberg |
| 6,718,985 B2 | 4/2004 | Hlavka |
| 6,719,767 B1 | 4/2004 | Kimblad |
| 6,723,038 B1 | 4/2004 | Schroeder |
| 6,726,716 B2 | 4/2004 | Marquez |
| 6,740,107 B2 | 5/2004 | Loeb |
| 6,746,471 B2 | 6/2004 | Mortier |
| 6,752,813 B2 | 6/2004 | Goldfarb |
| 6,755,777 B2 | 6/2004 | Schweich, Jr. |
| 6,764,510 B2 | 7/2004 | Vidlund |
| 6,767,349 B2 | 7/2004 | Ouchi |
| 6,770,083 B2 | 8/2004 | Seguin |
| 6,797,001 B2 | 9/2004 | Mathis |
| 6,797,002 B2 | 9/2004 | Spence |
| 6,860,179 B2 | 3/2005 | Hopper |
| 6,875,224 B2 | 4/2005 | Grimes |
| 6,926,715 B1 | 8/2005 | Hauck |
| 6,945,978 B1 | 9/2005 | Hyde |
| 6,949,122 B2 | 9/2005 | Adams |
| 6,966,914 B2 | 11/2005 | Abe |
| 6,986,775 B2 | 1/2006 | Morales |
| 7,004,970 B2 | 2/2006 | Cauthen, III |
| 7,011,669 B2 | 3/2006 | Kimblad |
| 7,048,754 B2 | 5/2006 | Martin |
| 7,112,207 B2 | 9/2006 | Allen |
| 7,226,467 B2 | 6/2007 | Lucatero |
| 7,288,097 B2 | 10/2007 | Seguin |
| 7,381,210 B2 | 6/2008 | Zarbatany |
| 7,464,712 B2 | 12/2008 | Oz |
| 7,497,822 B1 | 3/2009 | Kugler |
| 7,533,790 B1 | 5/2009 | Knodel |
| 7,563,267 B2 | 7/2009 | Goldfarb |
| 7,563,273 B2 | 7/2009 | Goldfarb |
| 7,604,646 B2 | 10/2009 | Goldfarb |
| 7,635,329 B2 | 12/2009 | Goldfarb |
| 7,651,502 B2 | 1/2010 | Jackson |
| 7,655,015 B2 | 2/2010 | Goldfarb |
| 7,655,040 B2 | 2/2010 | Douk |
| 7,666,204 B2 | 2/2010 | Thornton |
| 7,811,296 B2 | 10/2010 | Goldfarb |
| 8,052,592 B2 | 11/2011 | Goldfarb |
| 8,348,963 B2 | 1/2013 | Wilson |
| 8,940,001 B2 | 1/2015 | Catanese, III |
| 9,572,666 B2 | 2/2017 | Basude |
| 10,076,327 B2 | 9/2018 | Ellis |
| 10,238,495 B2 | 3/2019 | Marsot |
| 10,390,943 B2 | 8/2019 | Hernandez |
| 10,548,614 B2 | 2/2020 | Hernández |
| 10,631,871 B2 | 4/2020 | Goldfarb |
| 10,646,229 B2 | 5/2020 | Goldfarb |
| 10,653,427 B2 | 5/2020 | Goldfarb |
| 10,667,815 B2 | 6/2020 | Krone |
| 10,667,823 B2 | 6/2020 | Goldfarb |
| 10,828,042 B2 | 11/2020 | Goldfarb |
| 10,893,941 B2 | 1/2021 | Wei |
| 11,096,691 B2 | 8/2021 | Krone |
| 2001/0004715 A1 | 6/2001 | Duran |
| 2001/0005787 A1 | 6/2001 | Oz |
| 2001/0010005 A1 | 7/2001 | Kammerer |
| 2001/0018611 A1 | 8/2001 | Solem |
| 2001/0022872 A1 | 9/2001 | Marui |
| 2001/0037084 A1 | 11/2001 | Nardeo |
| 2001/0039411 A1 | 11/2001 | Johansson |
| 2001/0044568 A1 | 11/2001 | Langberg |
| 2002/0013571 A1 | 1/2002 | Goldfarb |
| 2002/0022848 A1 | 2/2002 | Garrison |
| 2002/0026233 A1 | 2/2002 | Shaknovich |
| 2002/0035361 A1 | 3/2002 | Houser |
| 2002/0035381 A1 | 3/2002 | Bardy |
| 2002/0042651 A1 | 4/2002 | Liddicoat |
| 2002/0055767 A1 | 5/2002 | Forde |
| 2002/0055774 A1 | 5/2002 | Liddicoat |
| 2002/0055775 A1 | 5/2002 | Carpentier |
| 2002/0058910 A1 | 5/2002 | Hermann |
| 2002/0058995 A1 | 5/2002 | Stevens |
| 2002/0077687 A1 | 6/2002 | Ahn |
| 2002/0087148 A1 | 7/2002 | Brock |
| 2002/0087169 A1 | 7/2002 | Brock |
| 2002/0087173 A1 | 7/2002 | Alferness |
| 2002/0103532 A1 | 8/2002 | Langberg |
| 2002/0107534 A1 | 8/2002 | Schaefer |
| 2002/0133178 A1 | 9/2002 | Muramatsu |
| 2002/0147456 A1 | 10/2002 | Diduch |
| 2002/0156526 A1 | 10/2002 | Hlavka |
| 2002/0158528 A1 | 10/2002 | Tsuzaki |
| 2002/0161378 A1 | 10/2002 | Downing |
| 2002/0169360 A1 | 11/2002 | Taylor |
| 2002/0183766 A1 | 12/2002 | Seguin |
| 2002/0183787 A1 | 12/2002 | Wahr |
| 2002/0183835 A1 | 12/2002 | Taylor |
| 2003/0005797 A1 | 1/2003 | Hopper |
| 2003/0045778 A1 | 3/2003 | Ohline |
| 2003/0050693 A1 | 3/2003 | Quijano |
| 2003/0069570 A1 | 4/2003 | Witzel |
| 2003/0069593 A1 | 4/2003 | Tremulis |
| 2003/0069636 A1 | 4/2003 | Solem |
| 2003/0074012 A1 | 4/2003 | Nguyen |
| 2003/0078654 A1 | 4/2003 | Taylor |
| 2003/0083742 A1 | 5/2003 | Spence |
| 2003/0105519 A1 | 6/2003 | Fasol |
| 2003/0105520 A1 | 6/2003 | Alferness |
| 2003/0120340 A1 | 6/2003 | Liska |
| 2003/0120341 A1 | 6/2003 | Shennib |
| 2003/0130669 A1 | 7/2003 | Damarati |
| 2003/0130730 A1 | 7/2003 | Cohn |
| 2003/0144697 A1 | 7/2003 | Mathis |
| 2003/0167071 A1 | 9/2003 | Martin |
| 2003/0171776 A1 | 9/2003 | Adams |
| 2003/0187467 A1 | 10/2003 | Schreck |
| 2003/0195562 A1 | 10/2003 | Collier |
| 2003/0208231 A1 | 11/2003 | Williamson |
| 2003/0225423 A1 | 12/2003 | Huitema |
| 2003/0229395 A1 | 12/2003 | Cox |
| 2003/0233038 A1 | 12/2003 | Hassett |
| 2004/0002719 A1 | 1/2004 | Oz |
| 2004/0003819 A1 | 1/2004 | St Goar |
| 2004/0019377 A1 | 1/2004 | Taylor |
| 2004/0019378 A1 | 1/2004 | Hlavka |
| 2004/0024414 A1 | 2/2004 | Downing |
| 2004/0030382 A1 | 2/2004 | St Goar |
| 2004/0039442 A1 | 2/2004 | St Goar |
| 2004/0039443 A1 | 2/2004 | Solem |
| 2004/0044350 A1 | 3/2004 | Martin |
| 2004/0044365 A1 | 3/2004 | Bachman |
| 2004/0049211 A1 | 3/2004 | Tremulis |
| 2004/0073302 A1 | 4/2004 | Rourke |
| 2004/0078053 A1 | 4/2004 | Berg |
| 2004/0087975 A1 | 5/2004 | Lucatero |
| 2004/0088047 A1 | 5/2004 | Spence |
| 2004/0092962 A1 | 5/2004 | Thornton |
| 2004/0097878 A1 | 5/2004 | Anderson |
| 2004/0097979 A1 | 5/2004 | Svanidze |
| 2004/0111099 A1 | 6/2004 | Nguyen |
| 2004/0122448 A1 | 6/2004 | Levine |
| 2004/0127981 A1 | 7/2004 | Rahdert |
| 2004/0127982 A1 | 7/2004 | MacHold |
| 2004/0127983 A1 | 7/2004 | Mortier |
| 2004/0133062 A1 | 7/2004 | Pai |
| 2004/0133063 A1 | 7/2004 | McCarthy |
| 2004/0133082 A1 | 7/2004 | Abraham-Fuchs |
| 2004/0133192 A1 | 7/2004 | Houser |
| 2004/0133220 A1 | 7/2004 | Lashinski |
| 2004/0133240 A1 | 7/2004 | Adams |
| 2004/0133273 A1 | 7/2004 | Cox |
| 2004/0138744 A1 | 7/2004 | Lashinski |
| 2004/0138745 A1 | 7/2004 | MacOviak |
| 2004/0148021 A1 | 7/2004 | Cartledge |
| 2004/0152847 A1 | 8/2004 | Emri |
| 2004/0152947 A1 | 8/2004 | Schroeder |
| 2004/0153144 A1 | 8/2004 | Seguin |
| 2004/0158123 A1 | 8/2004 | Jayaraman |
| 2004/0162610 A1 | 8/2004 | Liska |
| 2004/0167539 A1 | 8/2004 | Kuehn |

(56) References Cited

U.S. PATENT DOCUMENTS

| | | |
|---|---|---|
| 2004/0186486 A1 | 9/2004 | Roue |
| 2004/0186566 A1 | 9/2004 | Hindrichs |
| 2004/0193191 A1 | 9/2004 | Starksen |
| 2004/0215339 A1 | 10/2004 | Drasler |
| 2004/0220593 A1 | 11/2004 | Greenhalgh |
| 2004/0220657 A1 | 11/2004 | Nieminen |
| 2004/0225300 A1 | 11/2004 | Goldfarb |
| 2004/0236354 A1 | 11/2004 | Seguin |
| 2004/0243229 A1 | 12/2004 | Vidlund |
| 2004/0249452 A1 | 12/2004 | Adams |
| 2004/0249453 A1 | 12/2004 | Cartledge |
| 2004/0260393 A1 | 12/2004 | Rahdert |
| 2005/0004583 A1 | 1/2005 | Oz |
| 2005/0004665 A1 | 1/2005 | Aklog |
| 2005/0004668 A1 | 1/2005 | Aklog |
| 2005/0021056 A1 | 1/2005 | St Goar |
| 2005/0021057 A1 | 1/2005 | St Goar |
| 2005/0021058 A1 | 1/2005 | Negro |
| 2005/0033446 A1 | 2/2005 | Deem |
| 2005/0038508 A1 | 2/2005 | Gabbay |
| 2005/0049698 A1 | 3/2005 | Bolling |
| 2005/0055089 A1 | 3/2005 | MacOviak |
| 2005/0059351 A1 | 3/2005 | Cauwels |
| 2005/0149014 A1 | 7/2005 | Hauck |
| 2005/0159810 A1 | 7/2005 | Filsoufi |
| 2005/0197694 A1 | 9/2005 | Pai |
| 2005/0197695 A1 | 9/2005 | Stacchino |
| 2005/0216039 A1 | 9/2005 | Lederman |
| 2005/0228422 A1 | 10/2005 | MacHold |
| 2005/0228495 A1 | 10/2005 | MacOviak |
| 2005/0251001 A1 | 11/2005 | Hassett |
| 2005/0267493 A1 | 12/2005 | Schreck |
| 2005/0273160 A1 | 12/2005 | Lashinski |
| 2005/0287493 A1 | 12/2005 | Novak |
| 2006/0004247 A1 | 1/2006 | Kute |
| 2006/0015003 A1 | 1/2006 | Moaddes |
| 2006/0020275 A1 | 1/2006 | Goldfarb |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay |
| 2006/0064115 A1 | 3/2006 | Allen |
| 2006/0064116 A1 | 3/2006 | Allen |
| 2006/0064118 A1 | 3/2006 | Kimblad |
| 2006/0089671 A1 | 4/2006 | Goldfarb |
| 2006/0089711 A1 | 4/2006 | Dolan |
| 2006/0135993 A1 | 6/2006 | Seguin |
| 2006/0184203 A1 | 8/2006 | Martin |
| 2006/0190036 A1 | 8/2006 | Wendel |
| 2006/0195012 A1 | 8/2006 | Mortier |
| 2006/0229708 A1 | 10/2006 | Powell |
| 2006/0252984 A1 | 11/2006 | Rahdert |
| 2006/0293701 A1 | 12/2006 | Ainsworth |
| 2007/0038293 A1 | 2/2007 | St Goar |
| 2007/0100356 A1 | 5/2007 | Lucatero |
| 2007/0118155 A1 | 5/2007 | Goldfarb |
| 2007/0129737 A1 | 6/2007 | Goldfarb |
| 2007/0162125 A1 | 7/2007 | LeBeau |
| 2007/0197858 A1 | 8/2007 | Goldfarb |
| 2007/0198082 A1 | 8/2007 | Kapadia |
| 2007/0213747 A1 | 9/2007 | Monassevitch |
| 2008/0039935 A1 | 2/2008 | Buch |
| 2008/0051703 A1 | 2/2008 | Thornton |
| 2008/0051807 A1 | 2/2008 | St Goar |
| 2008/0097489 A1 | 4/2008 | Goldfarb |
| 2008/0167714 A1 | 7/2008 | St Goar |
| 2008/0183194 A1 | 7/2008 | Goldfarb |
| 2009/0156995 A1 | 6/2009 | Martin |
| 2009/0163934 A1 | 6/2009 | Raschdorf, Jr. |
| 2009/0177266 A1 | 7/2009 | Powell |
| 2009/0182419 A1 | 7/2009 | Bolling |
| 2009/0198322 A1 | 8/2009 | Deem |
| 2009/0270858 A1 | 10/2009 | Hauck |
| 2009/0326567 A1 | 12/2009 | Goldfarb |
| 2010/0016958 A1 | 1/2010 | St Goar |
| 2010/0152753 A1 | 6/2010 | Menn |
| 2012/0065464 A1 | 3/2012 | Ellis |
| 2012/0296349 A1 | 11/2012 | Smith |
| 2013/0035759 A1 | 2/2013 | Gross |
| 2013/0066341 A1 | 3/2013 | Ketai |
| 2013/0066342 A1 | 3/2013 | Dell |
| 2013/0073029 A1 | 3/2013 | Shaw |
| 2013/0253642 A1 | 9/2013 | Brecker |
| 2013/0261638 A1 | 10/2013 | Diamant |
| 2014/0066693 A1 | 3/2014 | Goldfarb |
| 2014/0067054 A1 | 3/2014 | Chau |
| 2014/0249553 A1 | 9/2014 | Kimura |
| 2014/0309670 A1 | 10/2014 | Bakos |
| 2015/0005809 A1 | 1/2015 | Ayres |
| 2015/0073473 A1 | 3/2015 | Broom |
| 2015/0257877 A1 | 9/2015 | Hernandez |
| 2016/0174979 A1 | 6/2016 | Wei |
| 2016/0287387 A1 | 10/2016 | Wei |
| 2017/0020521 A1 | 1/2017 | Krone |
| 2018/0146966 A1 | 5/2018 | Hernández |
| 2018/0161159 A1 | 6/2018 | Lee |
| 2020/0281591 A1 | 9/2020 | Krone |
| 2021/0346023 A1 | 11/2021 | Krone |

FOREIGN PATENT DOCUMENTS

| | | |
|---|---|---|
| CN | 103826548 | 5/2014 |
| CN | 103841899 | 6/2014 |
| CN | 107666868 | 2/2018 |
| DE | 3504292 C1 | 7/1986 |
| DE | 19810696 C1 | 5/1999 |
| DE | 10116168 A1 | 11/2001 |
| EP | 0179562 B1 | 7/1989 |
| EP | 0684012 A2 | 11/1995 |
| EP | 0727239 A2 | 8/1996 |
| EP | 0782836 A1 | 7/1997 |
| EP | 0558031 B1 | 4/1999 |
| EP | 1199037 A2 | 4/2002 |
| EP | 1230899 A1 | 8/2002 |
| EP | 1674040 A2 | 6/2006 |
| FR | 2768324 A1 | 3/1999 |
| GB | 1598111 A | 9/1981 |
| GB | 2151142 A | 7/1985 |
| JP | 09253030 A | 9/1997 |
| JP | 11089937 A | 4/1999 |
| JP | 2000283130 A | 10/2000 |
| JP | 2015502548 A | 1/2015 |
| WO | 8100668 A1 | 3/1981 |
| WO | 1981000668 | 3/1981 |
| WO | 9101689 A1 | 2/1991 |
| WO | 1991001689 | 2/1991 |
| WO | 9118881 A1 | 12/1991 |
| WO | 1991018881 | 12/1991 |
| WO | 9212690 A1 | 8/1992 |
| WO | 1992012690 | 8/1992 |
| WO | 9418881 A1 | 9/1994 |
| WO | 94018893 A1 | 9/1994 |
| WO | 1994018881 | 9/1994 |
| WO | 1994018893 | 9/1994 |
| WO | 9511620 A2 | 5/1995 |
| WO | 1995011620 | 5/1995 |
| WO | 9515715 A1 | 6/1995 |
| WO | 1995015715 | 6/1995 |
| WO | 9614032 A1 | 5/1996 |
| WO | 1996014032 | 5/1996 |
| WO | 9620655 A1 | 7/1996 |
| WO | 1996020655 | 7/1996 |
| WO | 9622735 A1 | 8/1996 |
| WO | 1996022735 | 8/1996 |
| WO | 9630072 A1 | 10/1996 |
| WO | 1996030072 | 10/1996 |
| WO | 9718746 A2 | 5/1997 |
| WO | 1997018746 | 5/1997 |
| WO | 9725927 A1 | 7/1997 |
| WO | 9726034 A1 | 7/1997 |
| WO | 1997025927 | 7/1997 |
| WO | 1997026034 A1 | 7/1997 |
| WO | 9738748 A2 | 10/1997 |
| WO | 9739688 A2 | 10/1997 |

(56) References Cited

FOREIGN PATENT DOCUMENTS

| | | |
|---|---|---|
| WO | 1997038748 | 10/1997 |
| WO | 1997039688 | 10/1997 |
| WO | 9748436 A2 | 12/1997 |
| WO | 1997048436 | 12/1997 |
| WO | 9807375 A1 | 2/1998 |
| WO | 1998007375 | 2/1998 |
| WO | 9824372 A1 | 6/1998 |
| WO | 1998024372 | 6/1998 |
| WO | 9830153 A1 | 7/1998 |
| WO | 9832382 A1 | 7/1998 |
| WO | 1998030153 | 7/1998 |
| WO | 1998032382 | 7/1998 |
| WO | 9835638 A1 | 8/1998 |
| WO | 9900059 A1 | 1/1999 |
| WO | 9901377 A1 | 1/1999 |
| WO | 1999000059 | 1/1999 |
| WO | 1999001377 | 1/1999 |
| WO | 9907354 A2 | 2/1999 |
| WO | 1999007354 | 2/1999 |
| WO | 9913777 A1 | 3/1999 |
| WO | 1999013777 | 3/1999 |
| WO | 9966967 A1 | 12/1999 |
| WO | 1999066967 | 12/1999 |
| WO | 0002489 A1 | 1/2000 |
| WO | 0003651 A1 | 1/2000 |
| WO | 0003759 A2 | 1/2000 |
| WO | 2000002489 | 1/2000 |
| WO | 2000003651 | 1/2000 |
| WO | 2000003759 | 1/2000 |
| WO | 0012168 A1 | 3/2000 |
| WO | 2000012168 | 3/2000 |
| WO | 0044313 A1 | 8/2000 |
| WO | 2000044313 | 8/2000 |
| WO | 0059382 A1 | 10/2000 |
| WO | 0060995 A2 | 10/2000 |
| WO | 2000059382 | 10/2000 |
| WO | 2000060995 | 10/2000 |
| WO | 0100111 A1 | 1/2001 |
| WO | 0100114 A1 | 1/2001 |
| WO | 0103651 A2 | 1/2001 |
| WO | 2001000111 | 1/2001 |
| WO | 2001000114 | 1/2001 |
| WO | 2001003651 | 1/2001 |
| WO | 0126557 A1 | 4/2001 |
| WO | 0126586 A1 | 4/2001 |
| WO | 0126587 A1 | 4/2001 |
| WO | 0126588 A2 | 4/2001 |
| WO | 0126703 A1 | 4/2001 |
| WO | 0128432 A1 | 4/2001 |
| WO | 0128455 A1 | 4/2001 |
| WO | 2001026557 | 4/2001 |
| WO | 2001026586 | 4/2001 |
| WO | 2001026587 | 4/2001 |
| WO | 2001026588 | 4/2001 |
| WO | 2001026703 | 4/2001 |
| WO | 2001028432 | 4/2001 |
| WO | 2001028455 | 4/2001 |
| WO | 0147438 A1 | 7/2001 |
| WO | 0149213 A2 | 7/2001 |
| WO | 0150985 A1 | 7/2001 |
| WO | 2001047438 | 7/2001 |
| WO | 2001049213 | 7/2001 |
| WO | 2001050985 | 7/2001 |
| WO | 0154618 A1 | 8/2001 |
| WO | 0156512 A1 | 8/2001 |
| WO | 2001054618 | 8/2001 |
| WO | 2001056512 | 8/2001 |
| WO | 0166001 A2 | 9/2001 |
| WO | 0170320 A1 | 9/2001 |
| WO | 2001066001 | 9/2001 |
| WO | 2001070320 | 9/2001 |
| WO | 0189440 A2 | 11/2001 |
| WO | 2001089440 | 11/2001 |
| WO | 0195831 A2 | 12/2001 |
| WO | 0195832 A2 | 12/2001 |
| WO | 0197741 A2 | 12/2001 |
| WO | 2001095831 | 12/2001 |
| WO | 2001095832 | 12/2001 |
| WO | 2001097741 | 12/2001 |
| WO | 0200099 A2 | 1/2002 |
| WO | 0201999 A2 | 1/2002 |
| WO | 0203892 A1 | 1/2002 |
| WO | 2002000099 | 1/2002 |
| WO | 2002001999 | 1/2002 |
| WO | 2002003892 | 1/2002 |
| WO | 2002034167 A2 | 5/2002 |
| WO | 02060352 A1 | 8/2002 |
| WO | 02062263 A2 | 8/2002 |
| WO | 02062270 A1 | 8/2002 |
| WO | 02062408 A2 | 8/2002 |
| WO | 2002060352 | 8/2002 |
| WO | 2002062263 | 8/2002 |
| WO | 2002062270 | 8/2002 |
| WO | 2002062408 | 8/2002 |
| WO | 03001893 A2 | 1/2003 |
| WO | 03003930 A1 | 1/2003 |
| WO | 2003001893 | 1/2003 |
| WO | 03020179 A1 | 3/2003 |
| WO | 2003020179 | 3/2003 |
| WO | 03028558 A2 | 4/2003 |
| WO | 2003028558 | 4/2003 |
| WO | 03037171 A2 | 5/2003 |
| WO | 2003037171 | 5/2003 |
| WO | 03047467 A1 | 6/2003 |
| WO | 03049619 A2 | 6/2003 |
| WO | 2003047467 | 6/2003 |
| WO | 2003049619 | 6/2003 |
| WO | 03073910 A2 | 9/2003 |
| WO | 03073913 A2 | 9/2003 |
| WO | 2003073910 | 9/2003 |
| WO | 2003073913 | 9/2003 |
| WO | 03082129 A2 | 10/2003 |
| WO | 2003082129 | 10/2003 |
| WO | 03105667 A2 | 12/2003 |
| WO | 2003105667 | 12/2003 |
| WO | 2004004607 A1 | 1/2004 |
| WO | 2004012583 A2 | 2/2004 |
| WO | 2004012789 A2 | 2/2004 |
| WO | 2004014282 A2 | 2/2004 |
| WO | 2004019811 A2 | 3/2004 |
| WO | 2004030570 A2 | 4/2004 |
| WO | 2004037317 A2 | 5/2004 |
| WO | 2004045370 A2 | 6/2004 |
| WO | 2004045378 A2 | 6/2004 |
| WO | 2004045463 A2 | 6/2004 |
| WO | 2004047679 A1 | 6/2004 |
| WO | 2004062725 A1 | 7/2004 |
| WO | 2004082523 A2 | 9/2004 |
| WO | 2004082538 A2 | 9/2004 |
| WO | 2004093730 A2 | 11/2004 |
| WO | 2004103162 A2 | 12/2004 |
| WO | 2004112585 A2 | 12/2004 |
| WO | 2004112651 A2 | 12/2004 |
| WO | 2005002424 A2 | 1/2005 |
| WO | 2005018507 A2 | 3/2005 |
| WO | 2005027797 A1 | 3/2005 |
| WO | 2005032421 A2 | 4/2005 |
| WO | 2005062931 A2 | 7/2005 |
| WO | 2005112792 A2 | 12/2005 |
| WO | 2006037073 A2 | 4/2006 |
| WO | 2006105008 A1 | 10/2006 |
| WO | 2006105009 A1 | 10/2006 |
| WO | 2006115875 A2 | 11/2006 |
| WO | 2006115876 A2 | 11/2006 |
| WO | 2007009099 A2 | 1/2007 |
| WO | 2007038608 A2 | 4/2007 |
| WO | 2009111802 | 9/2009 |
| WO | 2011034973 A2 | 3/2011 |
| WO | 2014138482 A1 | 9/2014 |
| WO | 2016161135 A1 | 10/2016 |
| WO | 2017015288 A2 | 1/2017 |

(56) References Cited

FOREIGN PATENT DOCUMENTS

| WO | 2018102310 A1 | 6/2018 |
| WO | 2018106482 A1 | 6/2018 |

OTHER PUBLICATIONS

U.S. Appl. No. 14/677,294, dated Dec. 17, 2018 Request for Continued Examination (RCE).
U.S. Appl. No. 14/677,294, dated Jul. 3, 2017 Restriction Requirement.
U.S. Appl. No. 14/677,294, dated Jul. 9, 2019 Notice of Allowance.
U.S. Appl. No. 14/677,294, dated Jun. 20, 2018 Notice of Allowance.
U.S. Appl. No. 14/677,294, dated Jun. 20, 2019 Response to Non-Final Office Action.
U.S. Appl. No. 14/677,294, dated Mar. 20, 2019 Non-Final Office Action.
U.S. Appl. No. 14/677,294, dated Mar. 6, 2018 Response to Non-Final Office Action.
U.S. Appl. No. 14/677,294, dated May 23, 2018 Notice of Allowance. 10 pages.
U.S. Appl. No. 14/677,294, dated Nov. 13, 2018 Notice of Allowance.
U.S. Appl. No. 14/677,294, dated Nov. 17, 2017 Non-Final Office Action. 19 pages.
U.S. Appl. No. 14/677,294, dated Oct. 25, 2018 Notice of Allowance.
U.S. Appl. No. 14/677,294, dated Sep. 20, 2019 Issue Fee Payment.
U.S. Appl. No. 14/677,294, dated Sep. 25, 2018 Notice of Allowance. 8 pages.
U.S. Appl. No. 14/805,275, now U.S. Pat. No. 10,667,815, filed Jul. 21, 2015 (Jun. 2, 2020).
U.S. Appl. No. 14/805,275, dated Apr. 19, 2019 Restriction Requirement.
U.S. Appl. No. 14/805,275, dated Apr. 20, 2020 Issue Fee Payment.
U.S. Appl. No. 14/805,275, dated Aug. 12, 2019 Response to Final Office Action.
U.S. Appl. No. 14/805,275, dated Aug. 5, 2019 Applicant Initiated Interview Summary.
U.S. Appl. No. 14/805,275, dated Dec. 7, 2017 Response to Restriction Requirement.
U.S. Appl. No. 14/805,275, dated Jan. 10, 2018 Non-Final Office Action.
U.S. Appl. No. 14/805,275, dated Jan. 21, 2020 Notice of Allowance.
U.S. Appl. No. 14/805,275, dated Jun. 11, 2019 Final Office Action.
U.S. Appl. No. 14/805,275, dated Jun. 7, 2018 Response to Non-Final Office Action.
U.S. Appl. No. 14/805,275, dated May 14, 2019 Response to Restriction Requirement.
U.S. Appl. No. 14/805,275, dated Nov. 12, 2019 Amendment and Request for Continued Examination (RCE).
U.S. Appl. No. 14/805,275, dated Nov. 30, 2018 Response to Restriction Requirement.
U.S. Appl. No. 14/805,275, dated Nov. 5, 2019 Advisory Action.
U.S. Appl. No. 14/805,275, dated Oct. 11, 2019 Response to Final Office Action.
U.S. Appl. No. 14/805,275, dated Oct. 16, 2019 Applicant Initiated Interview Summary.
U.S. Appl. No. 14/805,275, dated Oct. 4, 2018 Restriction Requirement.
U.S. Appl. No. 14/805,275, dated Oct. 6, 2017 Restriction Requirement.
U.S. Appl. No. 14/805,275, dated Sep. 25, 2019 Advisory Action.
U.S. Appl. No. 14/805,275, dated Sep. 25, 2019 Applicant Initiated Interview Summary.
U.S. Appl. No. 16/883,382.
Uchida et al., "Percutaneous cardiomyotomy and valvultomy with angioscopic guidance," Am. Heart J.(1991) 121:1221-1224.
Umana et al., 'Bow-Tie' Mitral Valve Repair: An Adjuvant Technique for Ischemic Mitral Regurgitation, Ann. Thorac. Surg., May 12, 1998, pp. 1640-1646, vol. 66.
Umana et al., "'Bow-tie' Mitral Valve Repair Successfully Addresses Subvalvular Dysfunction in Ischemic Mitral Regurgitation," Surgical Forum, XLVIII:279-280 (1997).
Votta et al., "3 D computational analysis of the stress distribution on the leaflets after edge to edge repair of mitral regurgitation," Journal of Heart Valve Disease(2002)11:810 822.
Abe et al. "De Vega's annuloplasty for acquired tricuspid disease: Early and late results in 110 patients" Ann. Thorac. Surg. (1989) 48:670-676.
Agricola et al., "Mitral valve reserve in double orifice technique: an exercise echocardiographic study," Journal of Heart Valve Disease(2002)11(5):637 643.
Alfieri et al., "An effective technique to correct anterior mitral leaflet prolapse," J Card Surg(1999) 14(6):468-470.
Alfieri et al., "Novel suture device for beating heart mitral leaflet approximation," Annals of Thoracic Surgery(2002) 74:1488 1493.
Alfieri et al., "The double orifice technique in mitral valve repair: a simple solution for complex problems," Journal of Thoracic Cardiovascular Surgery(2001)122:674 681.
Alfieri et al., "The edge to edge technique," The European Association for Cardio-Thoracic Surgery 14th Annual Meeting, (2000) Oct. 7-11 Book of Proceedings. 3 pages.
Alfieri, "The edge-to-edge repair of the mitral valve," [Abstract] 6th Annual NewEra Cardiac Care: Innovation & Tecnology, Heart Surgery Forum(2003) pp. 103.
Alvarez et al., "Repairing the degenerative mitral valve: Ten-to fifteen-year follow-up" J. Thorac. Cardiovasc. Surg. (1996) 112:238-247.
Arisi et al., "Mitral valve repair with Alfieri technique in mitral regurgitation of diverse etiology: early echocardiographic results," Circulation Supplement II(2001) 104(17):3240.
Bach et al., "Early improvement in congestive heart failure after correction of secondary mitral regurgitation in end- stage cardiomyopathy," Am. Heart J.(1995) 129:1165-1170.
Bach et al., "Improvement following correction of secondary mitral regurgitation in end-stage cardiomyopathy with mitral annuloplasty" Am. J. Cardiol.(1996) 78:966-969.
Bailey, "Surgery of the Heart," Chapter 20(1995) pp. 686-737.
Bernal et al."The 'Valve Racket': a new and different concept of atrioventricular valve repair," Eur. J. Cardio-thoracic Surgery 29:1026-29 (2006).
Bhudia et al., "Edge-to-edge (Alfieri) mitral repair: results in diverse clinical settings," Ann Thorac Surg, 77: 1598-1606 (2004).
Bhudia, #58 Edge-to-edge mitral repair: a versatile mitral repair technique, 2003 STS Presentation[Abstract Only]. 2 pages.
Bolling et al., Surgery for Acquired Heart Disease: Early Outcome of Mitral Valve Reconstruction in Patients with End-stage Cardiomyopathy, J. Thor. and Cariovasc. Surg., Apr. 1995, pp. 676-683, vol. 109.
Borghetti et al., "Preliminary observations on haemodynamics during physiological stress conditions following 'double-orifice' mitral valve repair," European Journal of Cardio-thoracic Surgery, Apr. 18(2001) 20:262-269.
Castedo, "Edge-to-Edge Tricuspid Repair for Redeveloped Valve Incompetence after DeVega's Annuloplasty," Ann Thora Surg., 75:605-606 (2003).
Chinese Office Action dated Sep. 9, 2013 in Application No. 200980158707.2 (with English translation) 11 pages.
Communication dated Apr. 16, 2018 from the European Patent Office in counterpart European application No. 04752603.3. 39 pages.
Communication dated Apr. 28, 2017 issued by the European Patent Office in counterpart application No. 16196023.2. 11 pages.
Communication dated Jan. 26, 2017, from the European Patent Office in counterpart European application No. 16196023.2. 7 pages.
Communication dated May 8, 2017, from the European Patent Office in counterpart European Application No. 04752714.8. 6 pages.

(56) References Cited

OTHER PUBLICATIONS

Dec et al., "Idiopathic dilated cardiomyopathy," N. Engl. J. Med. (1994) 331:1564-1575. 12 pages.
Dottori et al., "Echocardiographic imaging of the Alfieri type mitral valve repair," Ital Heart J(2001) 2(4):319-320.
Downing et al., "Beating heart mitral valve surgery: Preliminary model and methodology," Journal of Thoracic and Cardiovascular Surgery(2002) 123(6):1141-1146.
Extended European Search Report, dated Oct. 17, 2014, issued in European Patent Application No. 06751584.1. 5 pages.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al. "Restoring Optimal Surface of Coaptation With a Mini Leaflet Prosthesis: A New Surgical Concept for the Correction of Mitral Velve Prolapse," Int'l. Soc. for Minimally Invasive Cardiothoracic Surgery 1(4):186-87 (2006).
Frazier et al., #62 Early Clinical Experience With An Implantable, Intracardiac Circulatory Support Device: Operative Considerations And Physiologic Implications, 2003 STS Presentation1 page total. [Abstract Only].
Fucci et al., Improved Results with Mitral Valve Repair Using New Surgical Techniques, Eur. J. Cardiothorac. Surg., Nov. 1995, pp. 621-627, vol. 9.
Fundaro et al., "Chordal plication and free edge remodeling for mitral anterior leaflet prolapse repair: 8-year follow-up," Annals of Thoracic Surgery(2001) 72:1515-1519.
Garcia-Rinaldi et al., "Left ventricular vol. reduction and reconstruction is ischemic cardiomyopathy," Journal of Cardiac Surgery(1999) 14:199-210.
Gateliene, "Early and postoperative results results of metal and tricuspid valve insufficiency surgical treatment using edge-to-edge central coaptation procedure," Medicina 38 (Suppl 2): 172-175 (2002) [Article in LithuanianEnglish summary on p. 174 of the article].
Gatti et al."The edge to edge technique as a trick to rescue an imperfect mitral valve repair," Eur J Cardiothorac Surg. (2002) 22(5):817 20.
Gillinov et al., "Is Minimally Invasive Heart Valve Surgery a Paradigm for the Future?" Current Cardiology Reports, 1:318-322 (1999).
Gundry et al., "Facile Mitral Valve Repair Utilizing Leaflet Edge Approximation: Midterm Results of the Alfieri Figure of Eight Repair," The Western Thoracic Surgical Association, Scientific Session (May 1999). 1 page.
Gupta et al., #61 Influence Of Older Donor Grafts On Heart Transplant Survival: Lack Of Recipient Effects, 2003 STS Presentation[Abstract Only]. 1 page.
Ikeda et al., "Batista's operation with coronary artery bypass grafting and mitral valve plasty for ischemic dilated cardiomyopathy," The Japanese Journal of Thoracic and Cardiovascular Surgery(2000) 48:746-749.
International Search Report and Written Opinion of PCT Application No. PCT/US2009/068023, dated Mar. 2, 2010, 10 pages total.
Izzat et al., "Early experience with partial left ventriculectomy in the Asia-Pacific Region," Annuals of Thoracic Surgery (1999) 67:1703-1707.
Källner et al., "Transaortic approach for the Alfieri Stitch," Ann Thorac Surg(2001) 71:378-380.
Kameda et al., Annuloplasty for Severe Mitral Regurgitation Due to Dilated Cardiomyopathy, Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al., "Blade atrial septostomy: Experience with the first 50 procedures" Cathet. Cardiovasc. Diagn(1991) 23:257-262.

Kherani et al., "Edge-to-edge mitral valve repair: the Columbia Presbyterian experience," Ann Thorac Surg2004; 78:73-76.
Konertz et at, "Results after partial left ventriculectomy in a European heart failure population," Journal of Cardiac Surgery(1999) 14(2):129-135.
Kron et al., "Surgical relocation of the posterior papillary muscle in chronic ischemic mitral regurgitation," Annals. of Thoracic Surgery(2002)74:600 601.
Krüger et al., "Edge to edge technique in complex mitral valve repair," Thorac Cardiovasc Surg, (2000) Thema: Posterhttp://www.thieme.de/thoracic/abstracts/abstracts/p-73.html.
Langer et al."Posterior mitral leaflet extensions: An adjunctive repair option for ischemic mitral regurgitation?," J. Thorac. Cardiovasc. Surf. 131:868-77 (2006).
Lorusso et al., "Double-Orifice" technique to repair extensive mitral valve excision following acute endocarditis, J Card Surg(1998) 13:24-26.
Lorusso et al., "The double-orifice technique for mitral valve construction: predictors of postoperative outcome," Eur J. Cardiothorac Surg(2001) 20(3):583-589.
Maisano et al., "The double orifice repair for Barlow Disease: a simple solution for a complex repair," Supplement I Circulation(1999) 100(18):1-94.
Maisano et al., "The double orifice technique as a standardized approach to treat mitral regurgitation due to severe myxomatous disease: surgical technique," European Journal of Cardiothoracic Surgery(2000) 17:201-215.
Maisano et al., "The edge-to-edge technique: A simplified method to correct mitral insufficiency" Eur. J. Cardiothorac. Surg.(1998) 13:240-246.
Maisano et al., "The hemodynamic effects of double-orifice valve repair for mitral regurgitation: a 3D computational model," European Journal of Cardio-thoracic Surgery(1999) 15:419-425.
Maisano et al., "Valve repair for traumatic tricuspid regurgitation," Eur J. Cardio-thorac Surg(1996) 10:867-873.
Mantovani et al., "Edge-to-edge repair of congenital familiar tricuspid regurgitation: case report," J. Heart Valve Dis. (2000) 9 (5):641-643.
McCarthy and Cosgrove et al. "Tricuspid Valve Reapir with the Cosgrove- Edwards Annuloplasty System," Ann. Thorac. Surg. 64:267-268 (1997).
McCarthy et al., "Partial left ventriculectomy and mitral valve repair for end-stage congestive heart failure," European Journal of Cardio-thoracic Surgery(1998) 13:337-343.
Moainie et al., Correction of traumatic tricuspid regurgitation using the double orifice technique, Annals of Thoracic Surgery(2002) 73:963 965.
Morales et al., "Development of an off bypass mitral valve repair," The Heart Surgery Forum #1999-4963(1999) 2 (2):115-120.
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al.., "Tricuspid Valve Incompetence Caused by Nonpenetrating Thoracic Trauma", Annals of Thoracic Surgery, 1991, 51 (2)320-322.
Osawa et al., "Partial Left Ventriculectomy in a 3-Year Old Boy with Dilated Cardiomyopathy," Japanese Journal of Thoracic and Cardiovascular Surg, 48:590-593 (2000).
Park et al."Clinical use of a blade atrial septostomy" Circulation (1978) 58:600-608.
Patel et al., #57 Epicardial Atrial Defibrillation: Novel Treatment Of Postoperative Atrial Fibrillation, 2003 STS Presentation[Abstract Only]. 1 page.
Privitera et al."Mitral Valve Repair: Clinical Outcome and Pathology; Circulation," (2002) 106:173.
Redaelli et al., "A Computational Study of the Hemodynamics After 'Edge-To-Edge' Mitral Valve Repair," Journal of Biomechanical Engineering, 123:565-570 (2001).
Reul, "Mital valve reconstruction for mitral insufficiency," Progress in Cardiovascular Diseases, (1997) vol. XXXIX, No. 6pp. 567-599.
Ricchi et al., Linear Segmental Annuloplasty for Mitral Valve Repair, Ann. Thorac. Surg., Jan. 7, 1997, pp. 1805-1806, vol. 63.

(56) References Cited

OTHER PUBLICATIONS

Robicsek et al., #60 The Bicuspid Aortic Valve: How Does It Function? Why Does It Fail?, 2003 STS Presentation [Abstract Only]. 1 page.
Supplemental European Search Report of EP Application No. 02746781, dated May 13, 2008, 3 pages total.
Supplementary European Search Report issued in European Application No. 05753261.6 dated Jun. 9, 2011, 3 pages total.
Tager et al., Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
Tamura et al., "Edge to Edge Repair for Mitral Regurgitation in a Patient with Chronic Hemodialysis: Report of A Case," Kyobu Geka. The Japanese Journal of Thoracic Surgery, 54(9):788-790 (2001).
Tibayan et al., #59 Annular Geometric Remodeling In Chronic Ischemic Mitral Regurgitation, 2003 STS Presentation [Abstract Only]. 2 pages.
Timek, "Edge-to-edge mitral repair: gradients and three-dimensional annular dynamics in vivo during inotropic stimulation," European Journal of Cardio-thoracic Surgery, (2001)19:431-437.
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery(1999) 15:119-126.
U.S. Appl. No. 14/216,787, filed Mar. 17, 2014, Basude et al.
U.S. Appl. No. 14/577,852, now U.S. Pat. No. 10,188,392, filed Dec. 19, 2014 (Jan. 29, 2019) Wei.
U.S. Appl. No. 14/577,852, filed Aug. 16, 2017 Amendment and Request for Continued Examination (RCE).
U.S. Appl. No. 14/577,852, dated Apr. 25, 2018, Notice of Allowance. 7 pages.
U.S. Appl. No. 14/577,852, dated Aug. 30, 2018 Supplemental Amendment.
U.S. Appl. No. 14/577,852, dated Jul. 25, 2018 Request for Continued Examination (RCE).
U.S. Appl. No. 14/577,852, dated May 16, 2017, Office Action. 7 pages.
U.S. Appl. No. 14/577,852, dated Oct. 20, 2016, Office Action. 7 pages.
U.S. Appl. No. 14/577,852, dated Sep. 14, 2018 Notice of Allowance.
U.S. Appl. No. 14/577,852, dated Sep. 7, 2017, Office Action. 8 pages.
U.S. Appl. No. 14/577,852, filed Dec. 13, 2018 Issue Fee Payment.
U.S. Appl. No. 14/577,852, filed Jan. 20, 2017 Response to Non-Final Office Action.
U.S. Appl. No. 14/577,852, filed Jul. 14, 2016 Restriction Requirement.
U.S. Appl. No. 14/577,852, filed Mar. 6, 2018 Response to Non-Final Office Action.
U.S. Appl. No. 14/577,852, filed May 15, 2018 Notice of Allowance.
U.S. Appl. No. 14/577,852, filed Sep. 14, 2016 Response to Restriction Requirement.
U.S. Appl. No. 14/577,852, filed Sep. 28, 2018 Notice of Allowance.
U.S. Appl. No. 14/677,294, now U.S. Pat. No. 10,524,912, filed Apr. 2, 2015 (Jan. 7, 2020).
U.S. Appl. No. 14/677,294, dated Aug. 22, 2018 Request for Continued Examination (RCE).

TISSUE GRASPING DEVICES AND RELATED METHODS

CROSS-REFERENCE TO RELATED APPLICATIONS

This application is a continuation application of U.S. patent application Ser. No. 17/384,233 filed on Jul. 23, 2021, which is a continuation application of U.S. application Ser. No. 16/883,382 filed on May 26, 2020, now U.S. Pat. No. 11,096,691, which is a continuation application of U.S. patent application Ser. No. 14/805,275 filed on Jul. 21, 2015, now U.S. Pat. No. 10,667,815, the contents of which are hereby incorporated by reference in their entireties.

BACKGROUND

The present disclosure relates generally to medical methods, devices, and systems. In particular, the present disclosure relates to methods, devices, and systems for the endovascular, percutaneous, or minimally invasive surgical treatment of bodily tissues, such as tissue approximation or valve repair. More particularly, the present disclosure relates to repair of valves of the heart and venous valves, and devices and methods for removing or disabling mitral valve repair components through minimally invasive procedures.

Surgical repair of bodily tissues often involves tissue approximation and fastening of such tissues in the approximated arrangement. When repairing valves, tissue approximation often includes coapting the leaflets of the valves in a therapeutic arrangement which may then be maintained by fastening or fixing the leaflets. Such fixation of the leaflets can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles themselves, or the left ventricular wall may be damaged or otherwise dysfunctional. Commonly, the valve annulus may be damaged, dilated, or weakened, limiting the ability of the mitral valve to close adequately against the high pressures of the left ventricle during systole.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bow-tie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

In some patients, a fixation device can be installed into the heart using minimally invasive techniques. The fixation device can hold the adjacent segments of the opposed valve leaflets together to reduce mitral valve regurgitation. One such device used to clip the anterior and posterior leaflets of the mitral valve together is the MitraClip® fixation device, sold by Abbott Vascular, Santa Clara, California, USA.

These fixation devices often include clips designed to grip and hold against tissue as the clip arms are moved and positioned against the tissue at the treatment site and then closed against the tissue. Such clips are designed to continue gripping the tissue as the fixation device is closed into a final position. In order to achieve this effect, such these clips are sometimes equipped with barbs or hooks to grip the tissue as the clip is flexed into position against the tissue.

However, some tissue fixation treatments require a fixation device to move through a wide range of grasping angles in order to be properly positioned relative to the target tissue and then to grasp the tissue and bring it to a closed position. This moving and plastically deforming components of the fixation device during pre-deployment, positioning, and closure of the device can lead to the weakening and premature degradation of the fixation device. Additionally, some tissue fixation treatments require that the fixation device maintain a degree of flexibility and mobility to allow a range of physiological movement even after the device has been properly placed and the target tissue has been properly fixed into the desired position, This can increase the risk of pre-mature failure of the device as continued plastic deformation of the flexing components (e.g., from the continuous opening and closing of valve leaflets) leads to unfavorable degradation of the device.

For at least these reasons, there is an ongoing need to provide alternative and/or additional methods, devices, and systems for tissue fixation that may provide beneficial elasticity and durability of the flexing components without unduly increasing the associated manufacturing costs of the flexing components. There is also a need to provide such methods, devices, and systems in a manner that does not limit the tissue gripping ability of the tissue fixation device. At least some of the embodiments disclosed below are directed toward these objectives.

BRIEF SUMMARY

At least one embodiment of the present disclosure relates to a tissue gripping device, the tissue gripping device including: a base section; and a first arm having a first end coupled to the base section, and a free end extending from the base section; wherein the base section and the arm are formed of a shape-memory material configured to exhibit superelasticity in a physiological environment.

At least one embodiment of the present disclosure relates to a tissue fixation system configured for intravascular delivery and for use in joining mitral valve tissue during treatment of the mitral valve, the system including: a body; a first and second distal element, each including a first end pivotally coupled to the body and extending to a free second end and a tissue engagement surface between the first and second end, the tissue engagement surface being configured to approximate and engage a portion of leaflets of the mitral valve; and a tissue gripping device formed of a shape-memory material, the tissue gripping device including a base section and a first arm and a second arm, each arm having a first end coupled to the base section and a free end extending from the base section, the first and second arms being disposed opposite one another and each arm being configured to cooperate with one of the first or second distal elements to form a space for receiving and holding a portion of mitral valve tissue therebetween.

At least one embodiment of the present disclosure relates to a method of gripping tissue, the method including: positioning a tissue gripping device near a target tissue, the tissue gripping device being formed from a shape-memory material and including a base section and a first arm and a second arm, each arm having a first end coupled to the base section and a free end extending from the base section, the first and second arms being disposed opposite one another; and moving the tissue gripping device from a pre-deployed configuration toward a deployed configuration, the first and second arms being configured to resiliently flex toward a relaxed configuration in a distal direction as the tissue gripping device is moved from a pre-deployed configuration toward a deployed configuration.

At least one embodiment of the present disclosure relates to a method of manufacturing a tissue gripping device, the method including: cutting one or more structural features into a strip or sheet stock material of a shape-memory alloy, the one or more structural features including a plurality of slotted recesses disposed at one or more side edges of the stock material; and heat shape setting one or more bend features into the stock material.

At least one embodiment of the present disclosure relates to a tissue fixation kit, the kit including: a tissue gripping system that includes an actuator rod, an actuator line, a first and second distal element, each including a first end pivotally coupled to the actuator rod and extending to a free second end and a tissue engagement surface between the first and second end, the first and second distal elements being positionable by the actuator rod, a tissue gripping device formed of a shape-memory material, the tissue gripping device including a base section, a first arm, and a second arm, each arm having a first end coupled to the base section and a free end extending from the base section, the tissue gripping device being positionable by the actuator line; a handle; and a delivery catheter having a proximal end and a distal end, the tissue gripping system being couplable to the distal end of the delivery catheter and the handle being couplable to the proximal end of the delivery catheter.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only illustrated embodiments of the disclosure and are therefore not to be considered limiting of its scope. Embodiments of the disclosure will be described and explained with additional specificity and detail through the use of the accompanying drawings in which.

DETAILED DESCRIPTION

I. Cardiac Physiology

Figure 1:
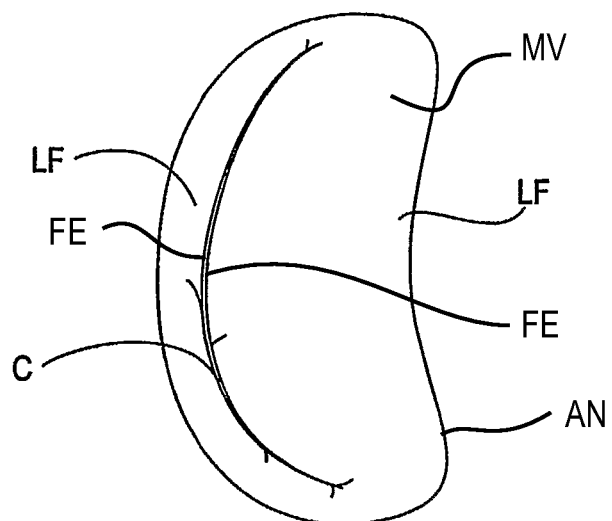
FIG. 1 illustrates free edges of leaflets of the mitral valve in normal coaptation.
Figure 2:
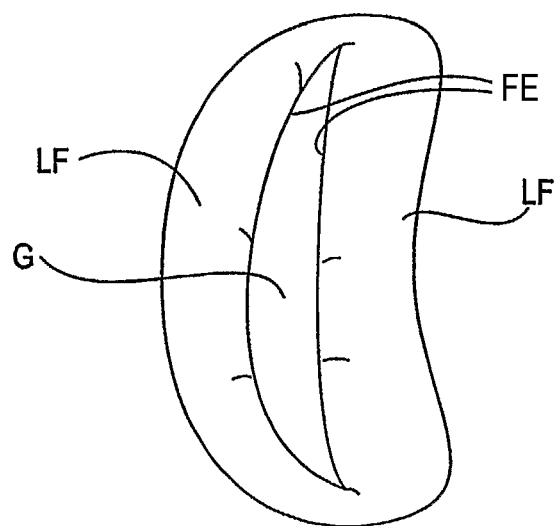
FIG. 2 illustrates the free edges in regurgitative coaptation.

As shown in FIG. 1, the mitral valve (MV) consists of a pair of leaflets (LF) having free edges (FE) which, in patients with normal heart structure and function, meet evenly to close along a line of coaption (C). The leaflets (LF) attach to the surrounding heart structure along an annular region called the annulus (AN). The free edges (FE) of the leaflets (LF) are secured to the lower portions of the left ventricle LV through chordae tendinae (or "chordae"). As the left ventricle of a heart contracts (which is called "systole"), blood flow from the left ventricle to the left atrium through the mitral valve (MV) (called "mitral regurgitation") is usually prevented by the mitral valve. Regurgitation occurs when the valve leaflets do not close properly and allow leakage from the left ventricle into the left atrium. A number of heart structural defects can cause mitral regurgitation. FIG. 2 shows a mitral valve with a defect causing regurgitation through a gap (G).

II. Exemplary Mitral Valve Fixation System

Several methods for repairing or replacing a defective mitral valve exist. Some defects in the mitral valve can be treated through intravascular procedures, where interventional tools and devices are introduced and removed from the heart through the blood vessels. One method of repairing certain mitral valve defects includes intravascular delivery of a fixation device to hold portions of the mitral valve tissues in a certain position. One or more interventional catheters may be used to deliver a fixation device to the mitral valve and install it there as an implant to treat mitral regurgitation.

Figure 3A:
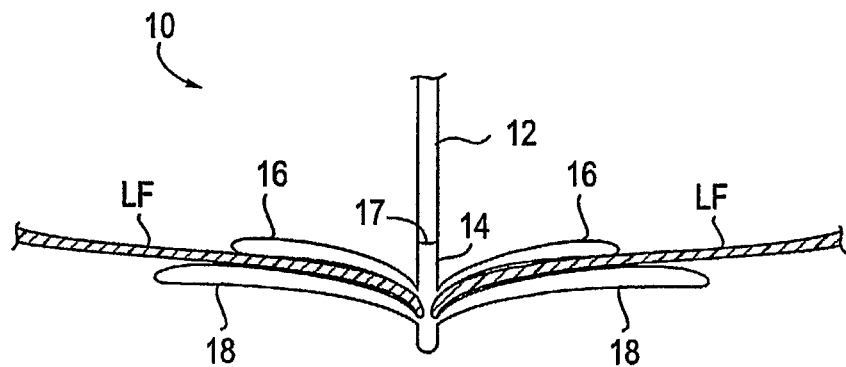
FIGS. 3A-3C illustrate grasping of the leaflets with an embodiment of a fixation assembly, inversion of the distal elements of the fixation assembly, and removal of the fixation assembly, respectively.

FIG. 3A illustrates a schematic of an interventional tool 10 or a tissue fixation system with a delivery shaft 12 and a fixation device 14. The tool 10 has approached the mitral valve MV from the atrial side and grasped the leaflets LF. The fixation device 14 is releasably attached to the shaft 12 of the interventional tool 10 at the distal end of the shaft 12. In this application, when describing devices, "proximal" means the direction toward the end of the device to be manipulated by the user outside the patient's body, and "distal" means the direction toward the working end of the device that is positioned at the treatment site and away from the user. When describing the mitral valve, proximal means the atrial side of the leaflets and distal means the ventricular side of the leaflets. The fixation device 14 includes grippers 16 and distal elements 18 which protrude radially outward and are positionable on opposite sides of the leaflets LF as shown so as to capture or retain the leaflets therebetween. The fixation device 14 is coupleable to the shaft 12 by a coupling mechanism 17.

Figure 3B:
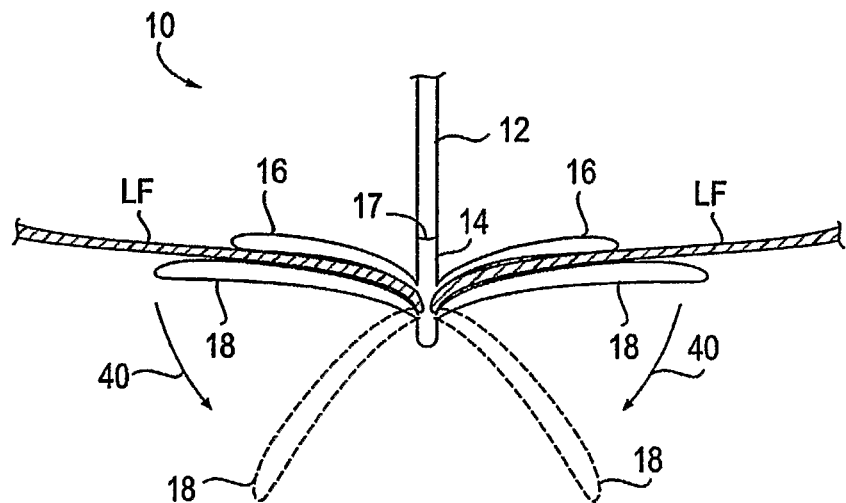

FIG. 3B illustrates that the distal elements 18 may be moved in the direction of arrows 40 to an inverted position.

Figure 3C:
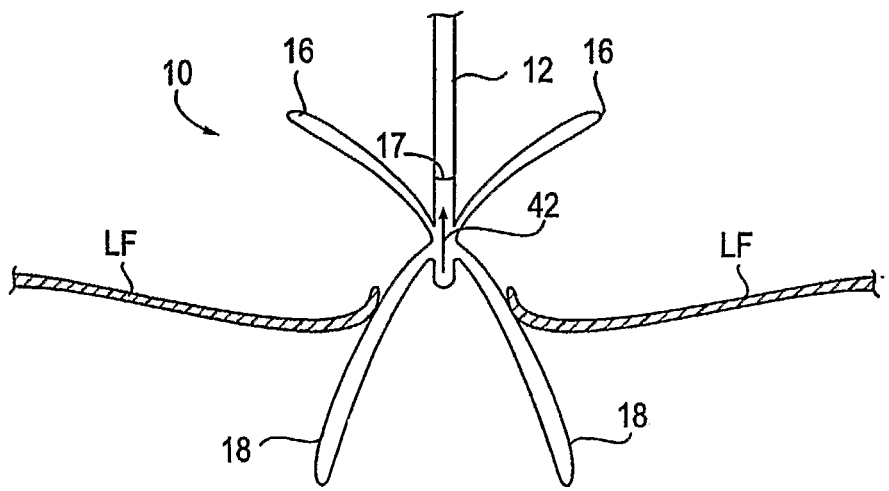

The grippers 16 may be raised as shown in FIG. 3C. In the inverted position, the device 14 may be repositioned and then be reverted to a grasping position against the leaflets as in FIG. 3A. Or, the fixation device 14 may be withdrawn (indicated by arrow 42) from the leaflets as shown in FIG. 3C. Such inversion reduces trauma to the leaflets and minimizes any entanglement of the device with surrounding tissues.

Figure 4:
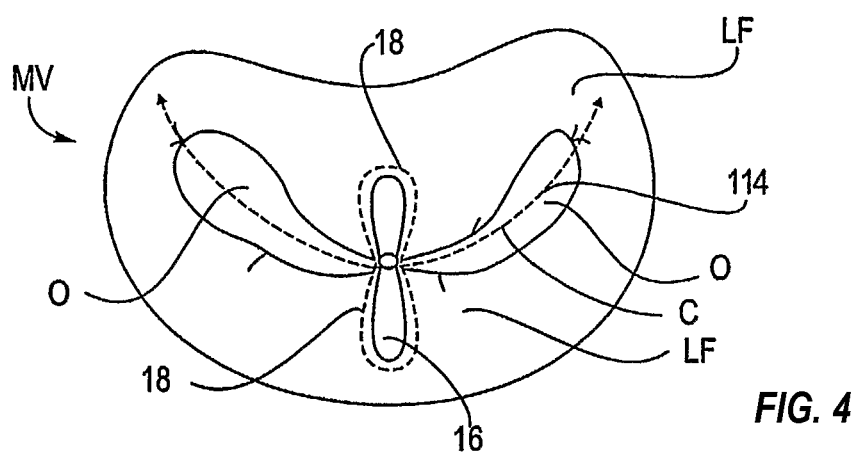
FIG. 4 illustrates the embodiment of a fixation assembly of FIGS. 3A-3C in a desired orientation relative to the leaflets.

FIG. 4 illustrates the fixation device 14 in a desired orientation in relation to the leaflets LF. The mitral valve MV is viewed from the atrial side, so the grippers 16 are shown in solid line and the distal elements 18 are shown in dashed line. The grippers 16 and distal elements 18 are positioned to be substantially perpendicular to the line of coaptation C. During diastole (when blood is flowing from the left atrium to the left ventricle), fixation device 14 holds the leaflets LF in position between the grippers 16 and distal elements 18 surrounded by openings or orifices O which result from the diastolic pressure gradient, as shown in FIG. 4. Once the leaflets are coapted in the desired arrangement, the fixation device 14 is detached from the shaft 12 and left behind as an implant.

Figure 5:
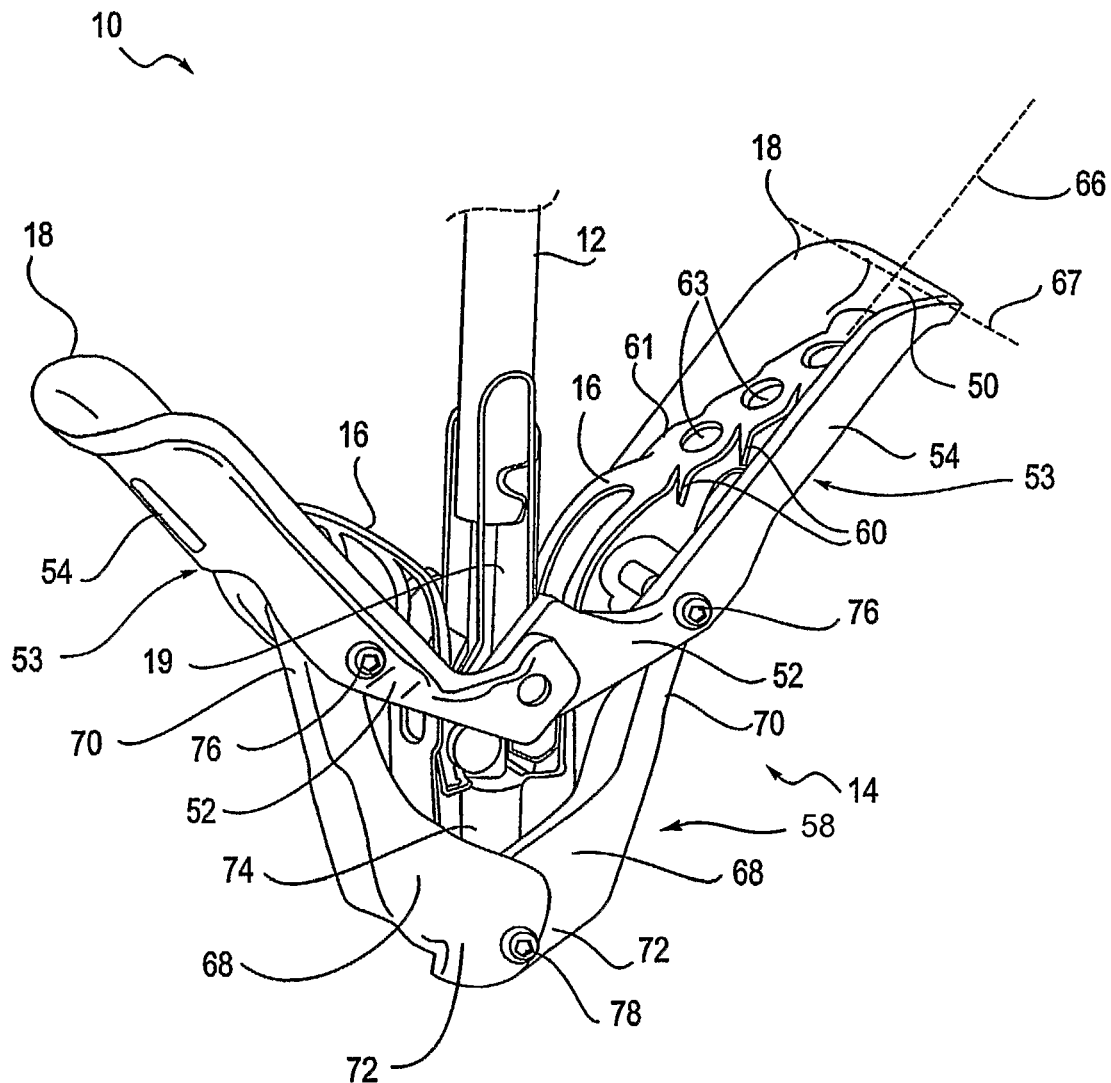
FIG. 5 illustrates an embodiment of a fixation assembly coupled to a shaft.

FIG. 5 illustrates an exemplary fixation device 14. The fixation device 14 is shown coupled to a shaft 12 to form an interventional tool 10. The fixation device 14 includes a coupling member 19, a gripper 16 having a pair of opposed arms, and a pair of opposed distal elements 18. The distal elements 18 include elongate arms 53, each arm having a proximal end 52 rotatably connected to the coupling member 19 and a free end 54. Preferably, each free end 54 defines a curvature about two axes, axis 66 perpendicular to longitudinal axis of elongate arms 53, and axis 67 perpendicular to axis 66 or the longitudinal axis of elongate arms 53. Elongate arms 53 have tissue engagement surfaces 50. Elongate arms 53 and tissue engagement surfaces 50 are configured to engage 4-10 mm of tissue, and preferably 6-8 mm, along the longitudinal axis of elongate arms 53. Elongate arms 53 further include a plurality of openings.

The arms of the gripper 16 are preferably resiliently biased toward the distal elements 18. When the fixation device 14 is in the open position, each arm of the gripper 16 is separated from the engagement surface 50 near the proximal end 52 of elongate arm 53 and slopes toward the engagement surface 50 near the free end 54 with the free end of the gripper 16 contacting engagement surface 50, as illustrated in FIG. 5. Arms of gripper 16 can include a plurality of openings 63 and scalloped side edges 61 to increase their grip on tissue. The arms of gripper 16 optionally include a frictional element or multiple frictional elements to assist in grasping the leaflets. The frictional elements may include barbs 60 having tapering pointed tips extending toward tissue engagement surfaces 50. Any suitable frictional elements may be used, such as prongs, windings, bands, barbs, grooves, channels, bumps, surface roughening, sintering, high-friction pads, coverings, coatings or a combination of these. The gripper 16 may be covered with a fabric or other flexible material. Preferably, when fabrics or coverings are used in combination with barbs or other frictional features, such features will protrude through such fabric or other covering so as to contact any tissue engaged by gripper 16.

The fixation device 14 also includes an actuator or actuation mechanism 58. The actuation mechanism 58 includes two link members or legs 68, each leg 68 having a first end 70 which is rotatably joined with one of the distal elements 18 at a riveted joint 76 and a second end 72 which is rotatably joined with a stud 74. The actuation mechanism 58 includes two legs 68 which are each movably coupled to a base 69. Or, each leg 68 may be individually attached to the stud 74 by a separate rivet or pin. The stud 74 is joinable with an actuator rod which extends through the shaft 12 and is axially extendable and retractable to move the stud 74 and therefore the legs 68 which rotate the distal elements 18 between closed, open, and inverted positions. Immobilization of the stud 74 holds the legs 68 in place and therefore holds the distal elements 18 in a desired position. The stud 74 may also be locked in place by a locking feature. This actuator rod and stud assembly may be considered a first means for selectively moving the distal elements between a first position in which the distal elements are in a collapsed, low profile configuration for delivery of the device, a second position in which the distal elements are in an expanded configuration for positioning the device relative to the mitral valve, and a third position in which the distal elements are secured in position against a portion of the leaflets adjacent the mitral valve on the ventricular side.

Figure 6A:
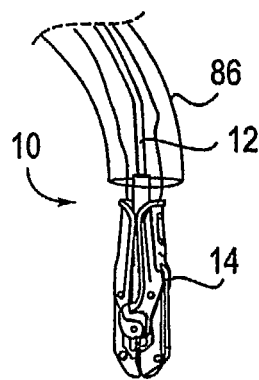
FIGS. 6A-6B, 7A-7C, and 8 illustrate an embodiment of a fixation assembly in various possible positions during introduction and placement of the assembly within the body to perform a therapeutic procedure.

FIGS. 6A-6B, 7A-7C, and 8 illustrate various possible positions of the fixation device 14 of FIG. 5. FIG. 6A illustrates an interventional tool 10 delivered through a catheter 86. The catheter 86 may take the form of a guide catheter or sheath. The interventional tool 10 comprises a fixation device 14 coupled to a shaft 12 and the fixation device 14 is shown in the closed position.

Figure 6B:
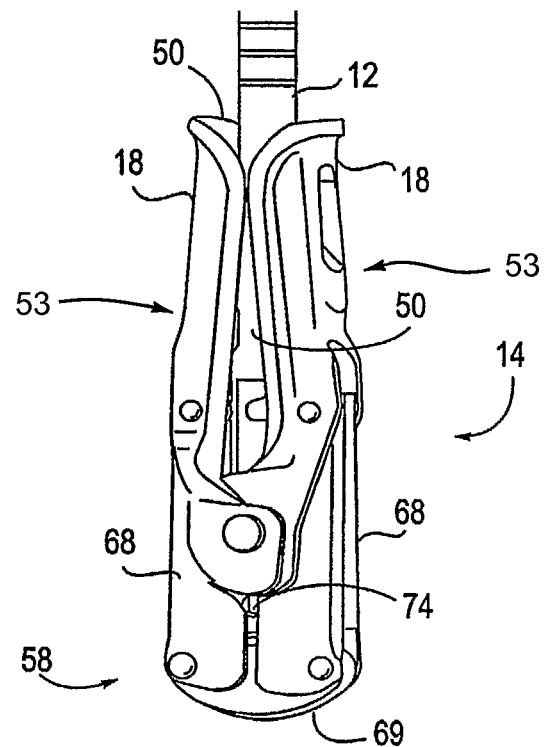

FIG. 6B illustrates a device similar to the device of FIG. 6A in a larger view. In the closed position, the opposed pair of distal elements 18 are positioned so that the tissue engagement surfaces 50 face each other. Each distal element 18 comprises an elongate arm 53 having a cupped or concave shape so that together the elongate arms 53 surround the shaft 12. This provides a low profile for the fixation device 14.

Figure 7A:
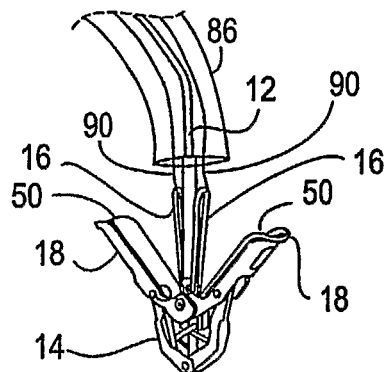
Figure 7B:
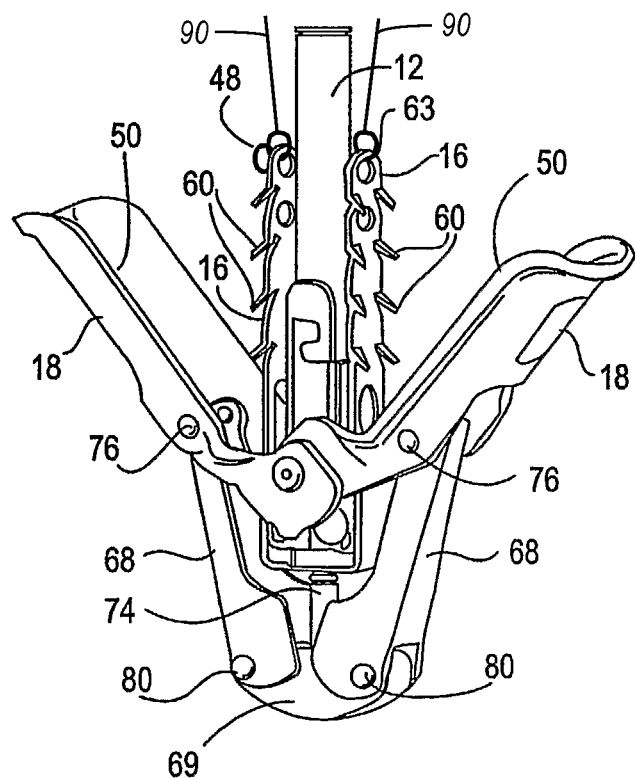
Figure 7C:
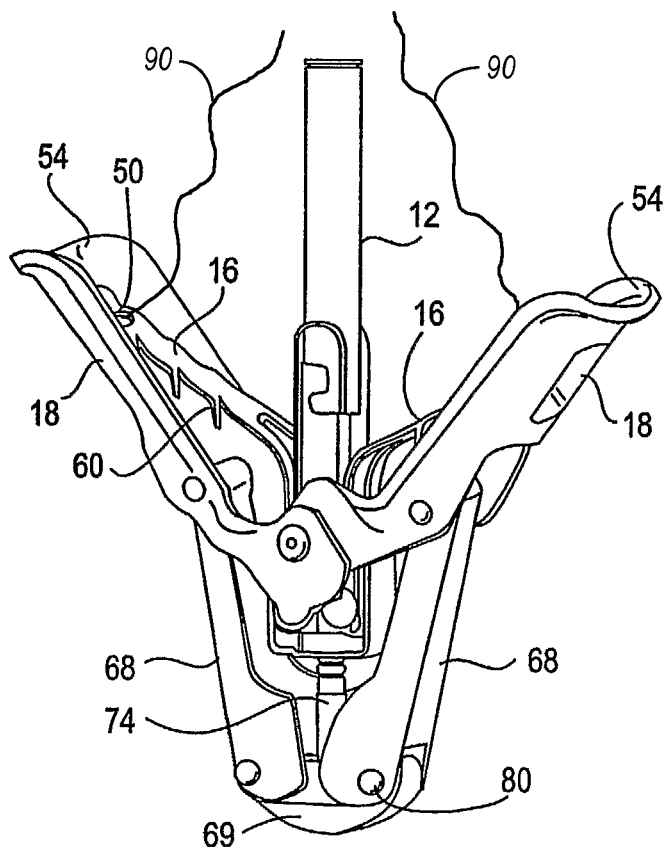

FIGS. 7A-7B illustrate the fixation device 14 in the open position. In the open position, the distal elements 18 are rotated so that the tissue engagement surfaces 50 face a first direction. Distal advancement of the actuator rod relative to shaft 12, and thus distal advancement of the stud 74 relative to coupling member 19, applies force to the distal elements 18 which begin to rotate around joints 76. Such rotation and movement of the distal elements 18 radially outward causes rotation of the legs 68 about joints 80 so that the legs 68 are directed slightly outwards. The stud 74 may be advanced to any desired distance correlating to a desired separation of the distal elements 18. In the open position, tissue engagement surfaces 50 are disposed at an acute angle relative to shaft 12, and can be at an angle of between 15 and 270 degrees relative to each other, preferably at an angle of between 45 and 225 degrees or between 90 and 180 degrees relative to each other (e.g., between 45 and 210 degrees, between 60 and 180 degrees, between 75 and 165 degrees, between 90 and 150 degrees, between 115 and 135 degrees, or 120 degrees). In the open position, the free ends 54 of elongate arms 53 may have a span therebetween of 1-40 mm, or 5-30 mm, usually 10-20 mm or 12-18 mm, and preferably 14-16 mm.

The arms of gripper 16 are typically biased outwardly toward elongate arms 53 when in a relaxed configuration. The arms of gripper 16 may be moved inwardly toward the shaft 12 and held against the shaft 12 with the aid of gripper lines 90 which can be in the form of sutures, wires, nitinol wire, rods, cables, polymeric lines, or other suitable structures. The gripper lines 90 can extend through a shaft of a delivery catheter (not shown) and connect with the gripper 16. The arms of the gripper 16 can be raised and/or lowered by manipulation of the gripper lines 90. For example, FIG.

7C illustrates gripper 16 in a lowered position as a result of releasing tension and/or providing slack to gripper lines 90. Once the device is properly positioned and deployed, the gripper lines can be removed by withdrawing them through the catheter and out the proximal end of the tool 10. The gripper lines 90 may be considered a second means for selectively moving the gripper 16 between a first position in which the gripper arms are in a collapsed, low profile configuration for delivery of the device and a second position in which the gripper arms are in an expanded configuration for engaging a portion of the leaflets adjacent the mitral valve on the atrial side.

In the open position, the fixation device 14 can engage the tissue which is to be approximated or treated. The interventional tool 10 is advanced through the mitral valve from the left atrium to the left ventricle. The distal elements 18 are then deployed by advancing actuator rod relative to shaft 12 to thereby reorient distal elements 18 to be perpendicular to the line of coaptation. The entire assembly is then withdrawn proximally and positioned so that the tissue engagement surfaces 50 contact the ventricular surface of the valve leaflets, thereby engaging the left ventricle side surfaces of the leaflets. The arms of the gripper 16 remain on the atrial side of the valve leaflets so that the leaflets lie between the proximal and distal elements. The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 8:
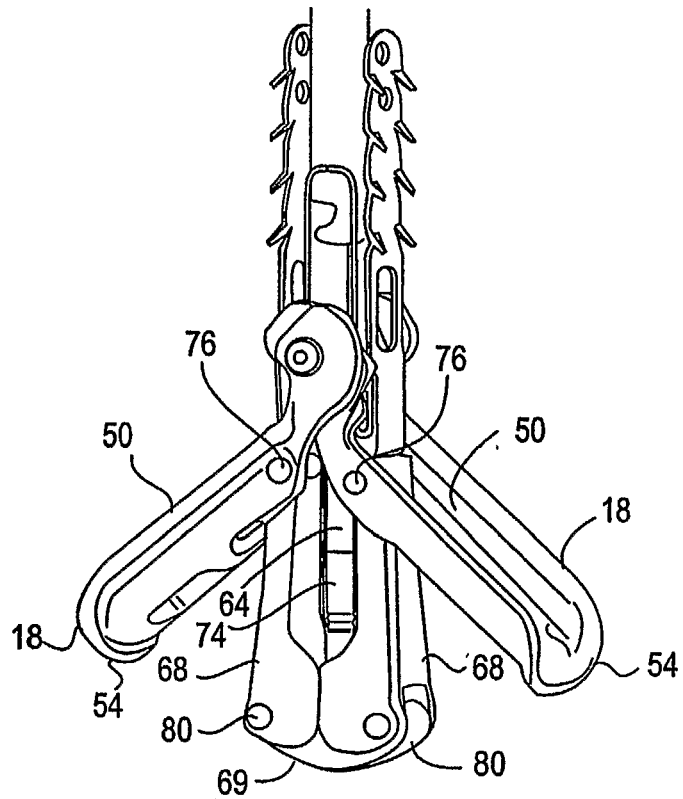

It may also be desired to invert distal elements 18 of the fixation device 14 to aid in repositioning or removal of the fixation device 14. FIG. 8 illustrates the fixation device 14 in the inverted position. By further advancement of actuator rod relative to shaft 12, and thus stud 74 relative to coupling member 19, the distal elements 18 are further rotated so that the tissue engagement surfaces 50 face outwardly and free ends 54 point distally, with each elongate arm 53 forming an obtuse angle relative to shaft 12.

The angle between elongate arms 53 when the device is inverted is preferably in the range of 180 to 360 degrees (e.g., 210 to 360 degrees, 240 to 360 degrees, 270 to 360 degrees, 300 to 360 degrees, or 330 to 360 degrees). Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than 40 mm, or no more than 30 mm or 20 mm, usually less than 16 mm, preferably 1-15 mm, 5-15 mm, or 10-15 mm, more preferably 12-14 mm. Barbs 60 are preferably angled in the distal direction (away from the free ends of the grippers 16), reducing the risk that the barbs will catch on or lacerate tissue as the fixation device is withdrawn.

Once the distal elements 18 of the fixation device 14 have been positioned in a desired location against the ventricle side surfaces of the valve leaflets, the leaflets may then be captured between the gripper 16 and the distal elements 18. The arms of the gripper 16 are lowered toward the tissue engagement surfaces 50 by releasing tension from gripper lines 90, thereby releasing the arms of the gripper 16 so that they are then free to move, in response to the internal spring bias force formed into gripper 16, from a constrained, collapsed position to an expanded, deployed position with the purpose of holding the leaflets between the gripper 16 and the distal elements 18. If regurgitation is not sufficiently reduced and/or if one or more of the leaflets are not properly engaged, the arms of the gripper 16 may be raised and the distal elements 18 adjusted or inverted to reposition the fixation device 14.

After the leaflets have been captured between the gripper 16 and distal elements 18 in a desired arrangement, the distal elements 18 may be locked to hold the leaflets in this position or the fixation device 14 may be returned to or toward a closed position. This is achieved by retraction of the stud 74 proximally relative to coupling member 19 so that the legs 68 of the actuation mechanism 58 apply an upwards force to the distal elements 18, which, in turn, rotate the distal elements 18 so that the tissue engagement surfaces 50 again face one another. The released grippers 16 which are biased outwardly toward distal elements 18 are concurrently urged inwardly by the distal elements 18. The fixation device 14 may then be locked to hold the leaflets in this closed position. The fixation device 14 may then be released from the shaft 12.

The fixation device 14 optionally includes a locking mechanism for locking the device 14 in a particular position, such as an open, closed, or inverted position, or any position therebetween. The locking mechanism may include a release harness. Applying tension to the release harness may unlock the locking mechanism. Lock lines can engage a release harnesses of the locking mechanism to lock and unlock the locking mechanism. The lock lines can extend through a shaft of the delivery catheter. A handle attached to the proximal end of the shaft can be used to manipulate and decouple the fixation device 14.

Additional disclosure regarding such fixation devices 14 may be found in PCT Publication No. WO 2004/103162 and U.S. patent application Ser. No. 14/216,787, the disclosures of both of which are incorporated by reference herein in their entirety.

III. Improved Gripping Device

Certain embodiments of tissue fixation devices of the present disclosure include a gripper formed from a shape-memory material. In preferred embodiments, the shape-memory material is configured to exhibit superelasticity when positioned in a physiological environment. Such shape-memory materials can include shape-memory alloys and/or shape-memory polymers. Shape-memory alloys included in embodiments of grippers of the present disclosure include copper-zinc-aluminum; copper-aluminum-nickel; nickel-titanium (NiTi) alloys known as nitinol; nickel-titanium platinum; and nickel-titanium palladium alloys, for example. Shape-memory polymers included in embodiments of grippers of the present disclosure include biodegradable polymers, such as oligo(c-caprolactone)diol, oligo(p-dioxanone)diol, and non-biodegradable polymers such as, polynorborene, polyisoprene, styrene butadiene, polyurethane-based materials, vinyl acetate-polyester-based compounds, for example. In preferred embodiments, the gripper is formed from nitinol. Such nitinol grippers can be configured with linear elastic properties, non-linear elastic properties, pseudo linear-elastic properties, or other elastic properties.

Figure 9A:
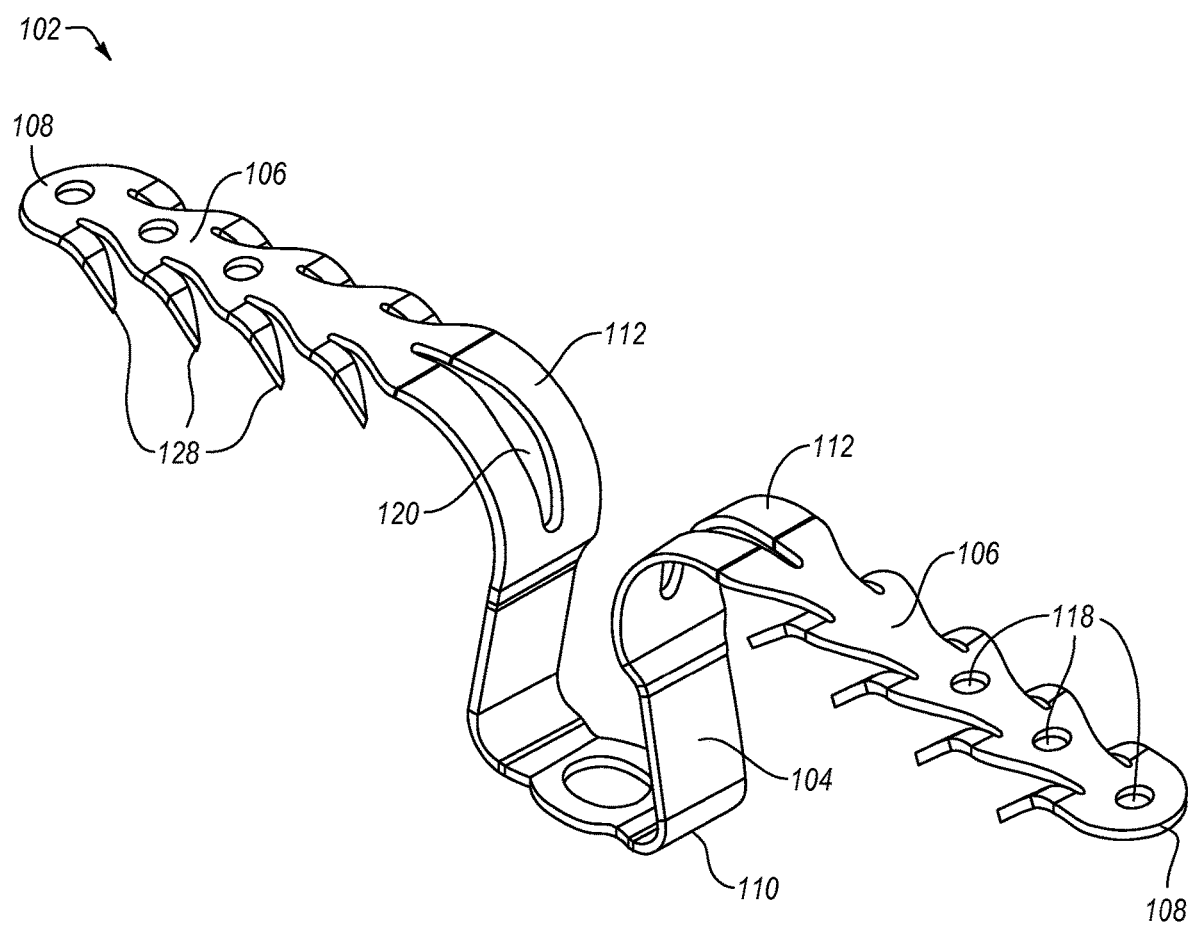
FIGS. 9A-9C illustrate various views of an embodiment of a tissue gripping device according to the present disclosure.
Figure 9B:
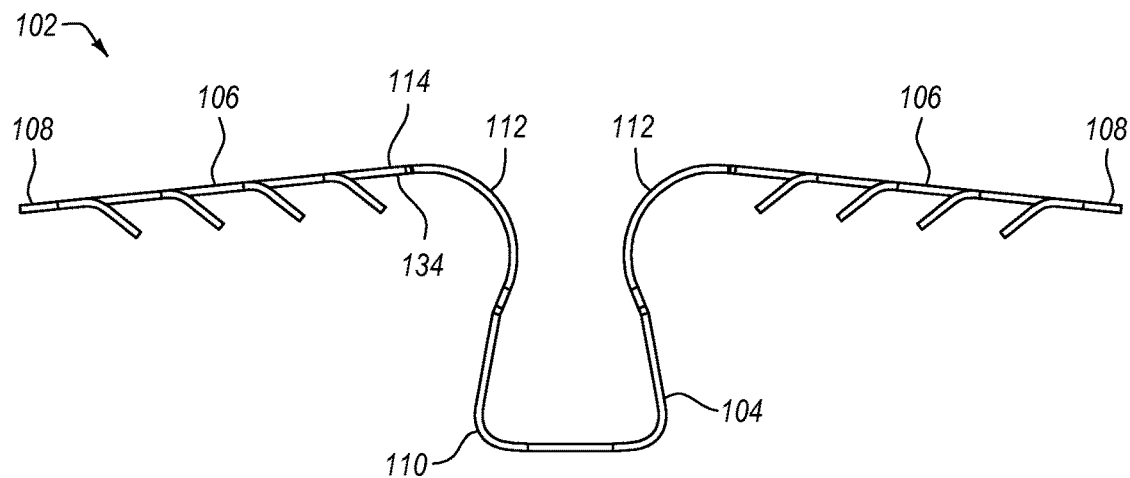
Figure 9C:
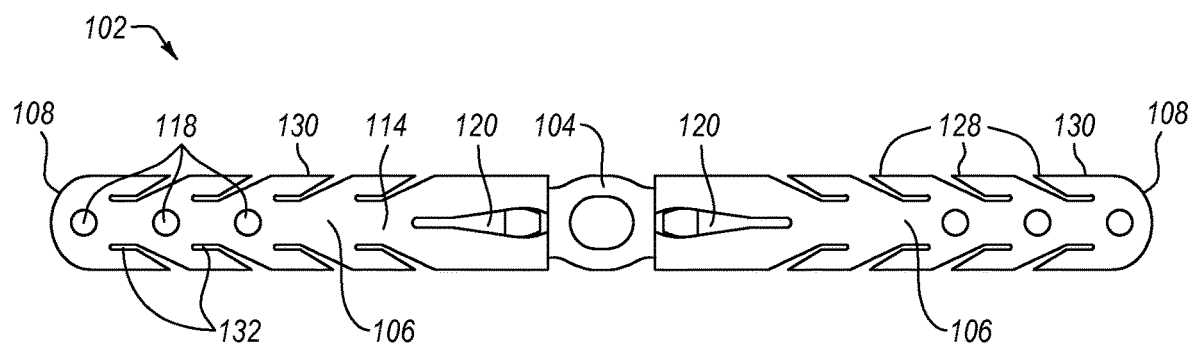

FIGS. 9A-9C illustrate various views of an embodiment of a tissue gripper 116 formed from a shape-memory material. In preferred embodiments, the tissue gripper 116 is formed from a nickel titanium alloy with transformation temperature (e.g., an austenite finish temperature ($A_f$)) of −5 to 37 degrees C., or from −5 to 30 degrees C., or from −5 to 27 degrees C., or from −5 to 25 degrees C., or from −5 to 20 degrees C., or from −5 to 15 degrees C., or from −5 to 10 degrees C., or from 0 to 10 degrees C. In such embodiments, the gripper 116 can exhibit superelasticity at physiological temperatures, and can exhibit superelasticity during flexing, bending, and/or other maneuvering of the gripper 116. For instance, the gripper 116 can exhibit superelasticity during positioning and deployment of the device at a treatment site and/or during continued movement after being deployed.

During a mitral valve repair procedure or other tissue fixing procedure, for example, portions of the tissue gripping device may need to repeatedly pass through wide angles as multiple tissue grasping attempts are made and/or as the gripper 116 is moved into an acceptable position against the leaflets of the mitral valve or against other targeted tissue. Furthermore, even after deployment, the tissue gripper 116 may need to provide some amount of flexibility and movement as the repaired and/or fixated tissue continues to flex and/or move. For example, one situation where additional flexibility and movement may be necessary is where mitral valve tissue continues to flex against the gripper 116 during cardiac cycles. In other situations, additional flexibility and movement may be necessary as the repaired and/or fixated tissue flexes, shifts, stretches, or otherwise moves relative to an original fixed position, such as with various musculoskeletal tissues during various forms of physiological movement (e.g., in response to muscle contraction and/or relaxation, movement at a joint, and movement between adjacent or nearby connective tissues).

Forming the tissue gripper 116 from a shape-memory material such as nitinol may avoid plastic deformation of the tissue gripper 116 during these movements. In preferred embodiments, the shape-memory material is configured to exhibit superelasticity at physiological temperatures, thereby enabling the tissue gripper 116 to stay entirely within the elastic deformation range throughout its life within the body. Even more preferably, the shape-memory material is configured to exhibit superelasticity throughout the range of temperatures expected to be encountered during pre-deployment, deployment, and implanted use within the body (e.g., 0 to 40 degrees C., 5 to 40 degrees C., 10 to 37 degrees C., 15 to 37 degrees C., 20 to 37 degrees C., and 22 to 37 degrees C.).

For instance, in some embodiments, the shape-memory material can be nitinol, and the nitinol can be configured to have a hysteresis curve that leaves the tissue gripper 116 within the elastic deformation range throughout its life and throughout the range of temperatures that are expected to be encountered during pre-deployment, deployment, and implanted use within the body, or during any other time where the tissue gripper 116 is flexed and/or deformed, such as during post manufacturing testing and/or positioning within a delivery system prior to delivery to target tissue. Such embodiments can advantageously reduce and/or eliminate mechanical fatigue and degradation of the tissue gripper 116 from repeated and/or high levels of plastic deformation. In addition, as will be explained in more detail below, embodiments of the present disclosure can promote easier tissue grasping during deployment and/or positioning of the tissue gripper 116.

In the illustrated embodiment, the tissue gripper 116 includes a proximal side 114, a distal side 134, a base section 104, and a pair of arms 106. Each arm 106 may extend from the base section 104 to a free end 108. In other embodiments, there may be one arm extending from a base section, or there may be more than two arms extending from a base section. For example, some embodiments may have multiple arms arrayed about a base section (e.g., in a radial fashion), and/or may include a first plurality of arms disposed opposite a second plurality of arms.

The gripper 116 of the illustrated embodiment includes a pair of base bend features 110 disposed at the base section 104, and a pair of arm bend features 112 partitioning the arms 106 from the base section 104. The base bend features 110 form angles of 90 degrees or just under 90 degrees (e.g., 15 to 165 degrees, 30 to 150 degrees, 45 to 135 degrees, 60 to 120 degrees, 70 to 110 degrees, or 80 to 100 degrees) as measured from the proximal side 114, and the arm bend features 112 form angles of 90 degrees or just under 90 degrees (e.g., 15 to 165 degrees, 30 to 150 degrees, 45 to 135 degrees, 60 to 120 degrees, 70 to 110 degrees, or 80 to 100 degrees) as measured from the distal side 134.

The base bend features 110 and arm bend features 112 are configured to give the tissue gripper 116 a bent configuration when the tissue gripper 116 is in a relaxed state, such that when the tissue gripper 116 is forced into a stressed state (e.g., by bending the tissue gripper 116 at one or more of the base and/or arm bend features 110 and 112), the tissue gripper 116 is resiliently biased toward the relaxed state.

For example, an arm 106 may be positioned at the arm bend feature 112 in a manner that flexes the arm 106 in a proximal direction and an inward direction, thereby flexing the arm 106 toward a straighter configuration (e.g., increasing the angle of the arm bend feature 112 as measured from the distal side 134). In such a position, the tissue gripper 116 is in a stressed state such that the arm 106 of the tissue gripper 116 is resiliently biased toward a distal direction and an outward direction. Other embodiments may omit one or more of the bend features, and other embodiments may include additional bend features. These and other embodiments may include bend features with differing bend angles when in a relaxed state. For example, some embodiments may include bend features that measure greater than 90 degrees or less than 90 degrees when in a relaxed state.

In another example, prior to moving the tissue gripper 116 into position in the mitral valve or into position near other targeted tissue, the tissue gripper may be positioned in a pre-deployed configuration (see, e.g., FIGS. 6A-7B and related discussion) by positioning the arm bend features 112 toward a straighter configuration. The tissue grippers of the present disclosure, such as illustrated tissue gripper 116, beneficially and advantageously can be moved into such a pre-deployed configuration without being plastically deformed at the arm bend features 112 and/or at other areas. Accordingly, tissue gripper 116 may move from such a pre-deployed configuration back toward a relaxed configuration by allowing the arms 106 to move distally and outwardly. In preferred embodiments, the relaxed configuration, after the tissue gripper 116 has been moved into a pre-deployed configuration and back, is the same or substantially the same as prior to the tissue gripper 116 being moved into the pre-deployed configuration and back (e.g., the angles at the arm bend features 112 in the relaxed configuration are unchanged, as opposed to being altered as a result of plastic deformation).

The tissue gripper 116 of the illustrated embodiment may include a plurality of holes 118 distributed along the length of each arm 106. The holes 118 may be configured to provide a passage or tie point for one or more sutures, wires, nitinol wires, rods, cables, polymeric lines, other such structures, or combinations thereof. As discussed above, these materials may be coupled to one or more arms 106 to operate as gripper lines (e.g., gripper lines 90 illustrated in FIGS. 7A-7C) for raising, lowering, and otherwise manipulating, positioning and/or deploying the tissue gripper 116. In some embodiments, for example, suture loops or other structures may be positioned at one or more of the holes 118, and one or more gripper lines may be threaded, laced, or otherwise passed through the suture loops. Such suture loops or other suture fastening structures may be wrapped and/or threaded a single time or multiple times before being tied, tightened, or otherwise set in place. For example, some suture lines may be wrapped repeatedly and/or may double back on themselves in order to strengthen or further secure the coupling of the suture loop to an arm 106.

Other embodiments may include a tissue gripper with more or less holes and/or with holes in other positions of the tissue gripper. For example, some embodiments may omit holes completely, and some embodiments may include only one hole and/or only one hole per arm. Other embodiments may include holes of different shapes and/or sizes, such as holes formed as slots, slits, or other shapes. In embodiments where more than one hole is included, the holes may be uniform in size, shape, and distribution or may be non-uniform in one or more of size, shape, and distribution.

Each arm 106 of the illustrated embodiment includes a furcated section 120. The furcated section 120 may extend from the base section 104 to a position farther along the arm 106 toward the free end 108 of the arm 106, as illustrated. In other embodiments, a furcated section may be positioned at other locations along an arm and/or base section. Other embodiments may include one or more furcated sections extending completely to the free end of an arm, thereby forming a bifurcated or fork-shaped arm. Other embodiments omit any furcated sections. The furcated sections 120 of the illustrated embodiment coincide with the arm bend features 112. The furcated sections 120 may be configured (e.g., in size, shape, spacing, position, etc.) so as to provide desired resiliency, fatigue resistance, and/or flexibility at the coinciding arm bend features 112.

As illustrated, the tissue gripper 116 includes a plurality of frictional elements 128 configured to engage with tissue at a treatment site and resist movement of tissue away from the tissue gripping member after the frictional elements 128 have engaged with the tissue. As shown in the illustrated embodiment, the frictional elements 128 are formed as angled barbs extending distally and inwardly from a side edge 130 of the arms 106 of the gripper 116. In this manner, tissue that is engaged with the frictional elements 128 of a tissue gripper 116 is prevented from moving proximally and outwardly relative to the tissue gripper 116.

The frictional elements 128 of the illustrated tissue gripper 116 protrude from a side edge 130 of each of the arms 106, thereby forming a plurality of slotted recesses 132 disposed along side edges 130 of each arm 106 at sections adjacent to the frictional elements 128. Other embodiments may include frictional elements of varying size, number, and/or shape. For example, in some embodiments the frictional elements may be formed as posts, tines, prongs, bands, grooves, channels, bumps, pads, or a combination of these or any other feature suitable for increasing friction and/or gripping of contacted tissue.

Embodiments of the devices, systems, and methods of the present disclosure can provide particular advantages and benefits in relation to a tissue gripping and/or tissue fixation procedure. For example, at least one embodiment of the devices, systems, and methods of the present disclosure can include moving and/or flexing a tissue gripper from a pre-deployed configuration toward a deployed configuration at a wider angle (e.g., angle in which the arms of the gripping device are separated) than that disclosed by the prior art, providing advantages such as better grasping ability, less tissue trauma, better grasping of separate portions of tissue simultaneously (e.g., opposing leaflets of the mitral valve), reduced slip-out of tissue during additional device movements or procedural steps (e.g., during a closing step), reduced grasping force required in order to grip the targeted tissue, or combinations thereof. In addition, tissue grippers of the present disclosure may be moved into a pre-deployed configuration without resulting plastic deformation affecting the range of grasping angles of the device.

In addition, at least one embodiment of the present disclosure can include increased resistance to mechanical fatigue than that disclosed by the prior art. For example, at least some of the tissue gripping devices of the present disclosure can be formed of a shape-memory material that provides resistance to progressive weakening of the device as a result of repeatedly applied and/or cyclic loads. For instance, as compared to a tissue gripping device not formed from a shape-memory material, at least some of the tissue gripping devices of the present disclosure have enhanced resistance to the formation of microscopic cracks and other stress concentrators (e.g., at grain boundaries or other discontinuity locations of the material).

Figure 10A:
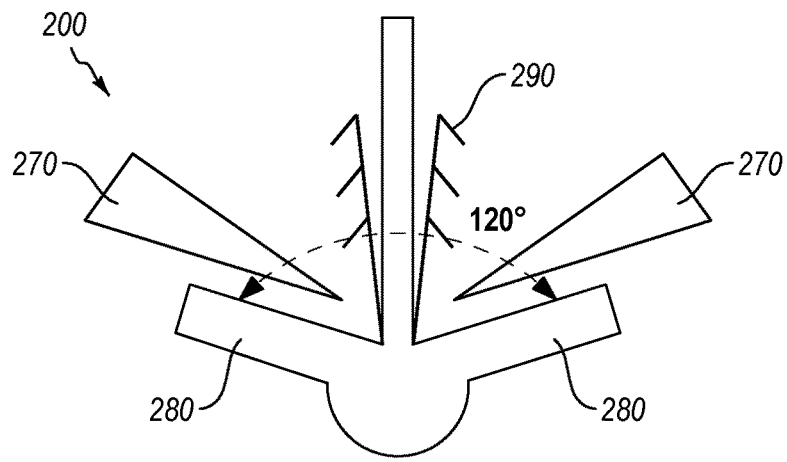
FIGS. 10A-10C illustrate a prior art tissue fixation method.
Figure 10B:
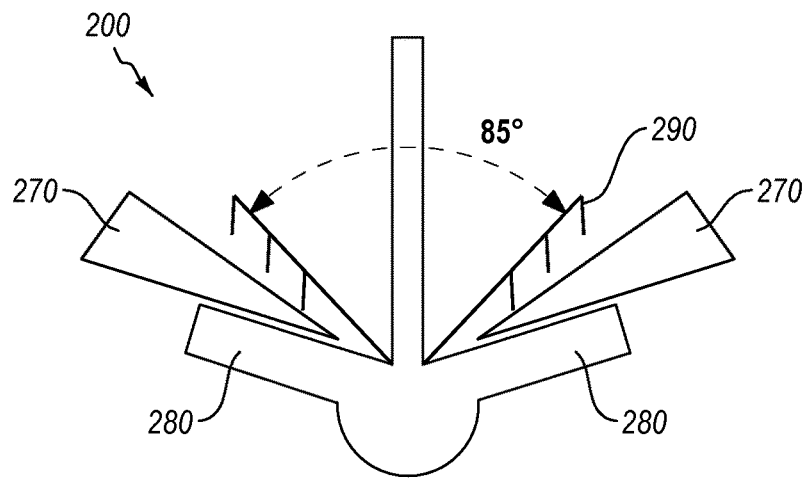
Figure 10C:
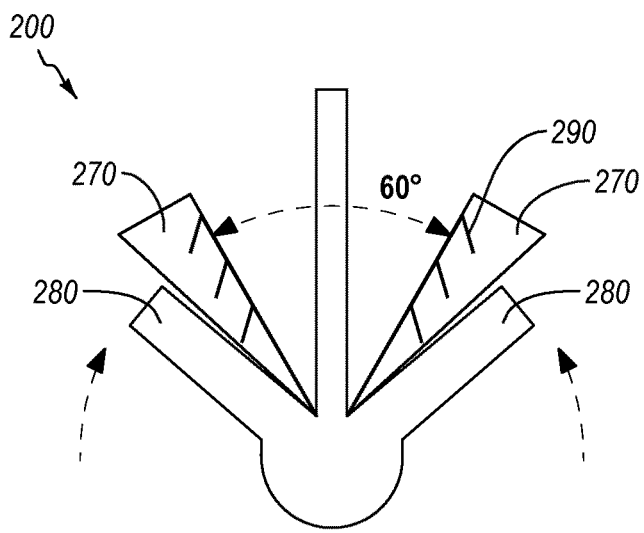

FIGS. 10A-10C illustrate a prior art gripping system 200 in use in a tissue gripping application. FIG. 10A shows a tissue gripper 290 made from a plastically deformable material positioned in a pre-deployed configuration. A pair of distal elements 280 is illustrated in an open position at 120 degrees, as measured from a proximal side, the pair of distal elements being positioned near target tissue 270 on the distal side of target tissue. Upon movement or release of the tissue gripper 290 from the pre-deployment configuration, the arms of the tissue gripper 290 move slightly in a proximal and outward direction toward the target tissue 270. However, the tissue gripper 290 is only able to reach a deployment angle, as measured by the separation of the opposing arms of the tissue gripper 290 on the proximal side, of 85 degrees. As illustrated in FIG. 10B, this may result in incomplete or missed grasping of the target tissue 270, as the arms of the tissue gripper 290 are unable to flex or extend outwardly and proximally far enough to fully engage with the target tissue 270.

As illustrated in FIG. 10C, gripping of the target tissue 270 requires at least an additional step of closing the distal elements 280 to 60 degrees in order to grip the target tissue 270 between the distal elements 280 and the arms of the tissue gripper 290 by moving the distal elements 280 proximally and inwardly toward the tissue gripper 290. During this step and/or during the interim between the position illustrated in FIG. 10B and the position illustrated in FIG. 10C, the target tissue 270 may move or slip away from the gripping system 200. In addition, the position of the target tissue 270 or portions of the target tissue 270 may shift relative to the tissue gripper 290 and/or the distal elements 280, requiring repositioning of the gripping system 200 and/or its components. This can be particularly problematic in procedures, such as mitral valve repair procedures, where the target tissue is rapidly and continuously moving, where multiple portions of target tissue must be grasped simultaneously, and where precise gripping position is demanded. Such limitations limit the number of available tissue gripping and/or fixation procedures and their effectiveness.

Figure 11A:
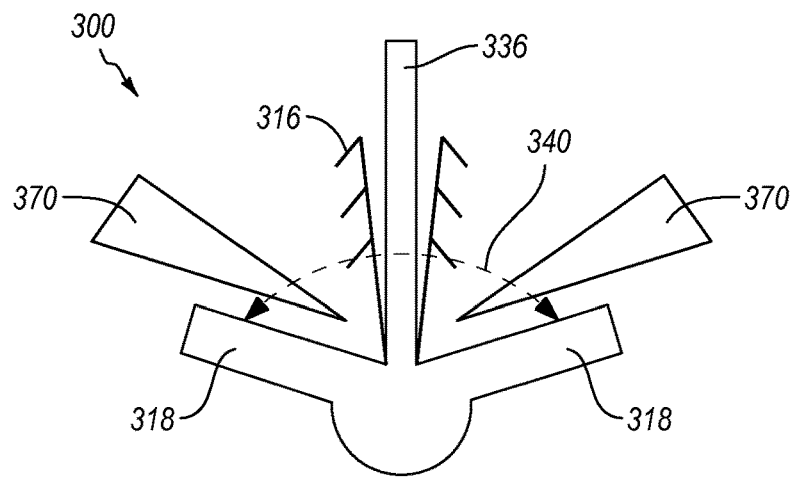
FIGS. 11A-11C illustrate an embodiment of a tissue fixation method and device.
Figure 11B:
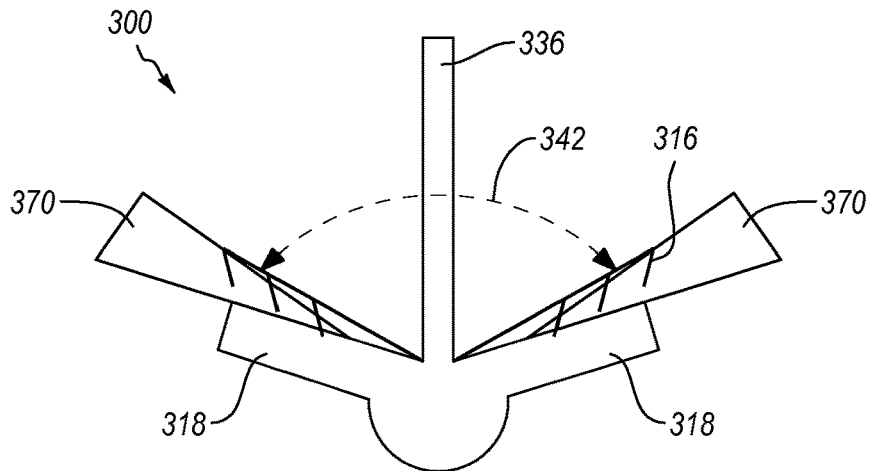
Figure 11C:
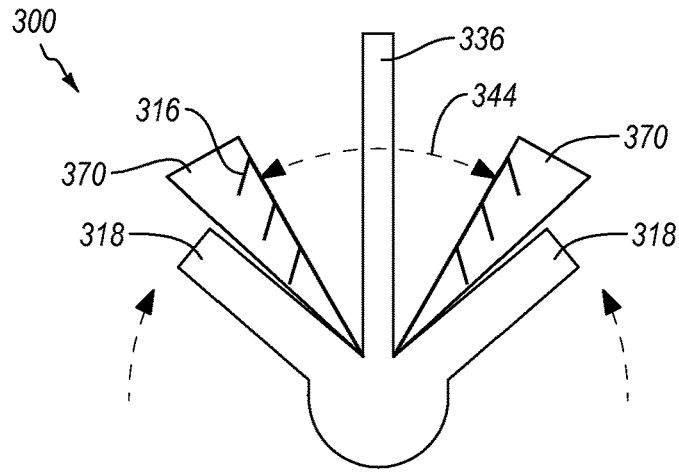

In contrast, FIGS. 11A-11C illustrate an embodiment of a tissue gripping system 300 of the present disclosure in a tissue gripping application. As illustrated in FIG. 11A, a pair of distal elements 318 are coupled to a body 336 (e.g., an actuator rod) and are associated with a tissue gripper 316. The tissue gripping system 300 may be positioned at or near target tissue 370, where the tissue gripper 316 can be positioned in a pre-deployed configuration with the arms of the tissue gripper 316 extending proximally from the base of the tissue gripper 316. In addition, the distal elements 318 may be moved to a distal side of the target tissue before, during, or after being positioned in an open configuration with an opening angle 340 of 120 degrees (e.g., 60 to 180 degrees, 75 to 165 degrees, 90 to 150 degrees, 105 to 135 degrees, 100 to 140 degrees, or 110 to 130 degrees). In other embodiments, the opening angle 340 may be more or less than 120 degrees (e.g., 60 to 90 degrees, or 90 to 120 degrees, or 120 to 150 degrees, or 150 to 180 degrees), though in preferred embodiments, the opening angle 340 is at least 120 degrees or more (e.g., 120 to 180 degrees). In some embodiments, the opening angle 340 can be more than 180 degrees (e.g., 190 degrees or 200 degrees or more).

As illustrated in FIG. 11B, after positioning the distal elements 318, the tissue gripper 316 can be moved and/or dropped from the pre-deployed configuration, where the arms of the tissue gripper 316 are positioned in a stressed state, toward a deployed configuration, where the arms flex and/or move toward a relaxed state. The tissue gripper 316 may be moved, dropped, or otherwise actuated using, for example, one or more gripper lines (such as those illustrated in FIGS. 7A-7C).

As illustrated in FIG. 11B, upon actuation, the tissue gripper 316 moves outwardly and distally to fully engage with the target tissue 370, and to fully engage the target tissue 370 against the proximal surface of the distal elements 318 by closing to an actuation angle 342 (as measured from the proximal side) that is substantially similar to the opening angle 340 of the distal elements 318. For example, the actuation angle 342 may equal the opening angle 340 or may be slightly smaller than the opening angle 340 (e.g., by 1 to 30 degrees, or 1 to 20 degrees, or 1 to 10 degrees, or 1 to 5 degrees or less) as a result of target tissue 370 being gripped between the distal elements 318 and the arms of the tissue gripper 316.

As shown by FIG. 11B, the full length of the arms of the tissue gripper 316 may be engaged against the target tissue 370 upon actuation of the tissue gripper 316 towards the deployed configuration. For example, because the actuation angle 342 is the same as or is substantially similar to the opening angle 340, any separation between the proximal surfaces of the distal elements 318 and the arms of the tissue gripper 316 is due to an amount of target tissue 370 caught and/or engaged between the arms of the tissue gripper 316 and a proximal surface of a distal element 318.

The tissue gripper 316 can be configured to provide an actuation angle 342 that is 90 to 180 degrees. In preferred embodiments, the actuation angle is 120 degrees (e.g., 60 to 180 degrees, 75 to 165 degrees, 90 to 150 degrees, 105 to 135 degrees, 100 to 140 degrees, or 110 to 130 degrees). In other embodiments, the actuation angle 342 may be more or less than 120 degrees (e.g., 60 to 90 degrees, or 90 to 120 degrees, or 120 to 150 degrees, or 150 to 180 degrees).

In preferred embodiments, the tissue gripper 316 is configured such that the arms of the tissue gripper 316 resiliently flex against target tissue 370 and/or distal elements 318 after moving from a pre-deployed configuration toward a deployed configuration. For example, the tissue gripper 316 can be configured such that, when positioned in a relaxed configuration, the arms of the tissue gripper 316 are open at an angle that is greater than a selected opening angle 340 of the distal elements 318. In some embodiments, for example, the arms of the tissue gripper 316, while positioned in a relaxed configuration, can be angled apart, as measured from a proximal side, at 180 degrees or slightly more than 180 degrees (e.g., 190 to 200 degrees). In such embodiments, the opening angle 340 of the distal elements 318 can be less than the angle between the arms of the tissue gripper 316 (e.g., 60 to 180 degrees, or 90 to 150 degrees, or 120 degrees). For example, when the opening angle 340 is 120 degrees, the actuation angle 344 of the tissue gripper 316 will expand to reach 120 degrees or beyond 120 degrees after moving toward a deployed configuration, but the arms of the tissue gripper 316 will not have moved to the full extent of the relaxed configuration. Thus, the arms of the tissue gripper 316, in such embodiments, will continue to resiliently flex against target tissue 370 and/or distal elements 318 even after expanding the full range of the actuation angle 344.

Accordingly, in such embodiments, when the tissue gripper 316 is moved from the pre-deployed configuration toward the deployed configuration, the arms of the tissue gripper 316 abut against the target tissue 370 and/or the distal elements 318 before reaching the full distal and outward extension of the relaxed configuration. In this manner, the arms of the tissue gripper 316 can resiliently flex against the target tissue 370 and/or distal elements 318 even after the tissue gripper 316 has moved the full or substantially full extent of the actuation angle 342.

In preferred embodiments, the tissue gripper 316, opening angle 340, and actuation angle 342 are configured such that when the tissue gripper 316 moves toward a deployed configuration and engages with target tissue 370, the tissue gripper 316 exerts a force of from 0.06 to 0.10 pounds against the target tissue 370. In other embodiments, the tissue gripper can exert a force of from 0.06 to 0.12 pounds or from 0.12 to 0.17 pounds, for example.

FIG. 11C illustrates that, in some embodiments, following movement of the tissue gripper 316 toward a deployed configuration, the distal elements 318 may be closed or partially closed in order to move or position the target tissue 370 and/or the components of the tissue gripping system 300 to a desired position and/or to assess the grasped tissue prior to further closing and release of the tissue gripping system 300. For example, the distal elements 318 can be actuated toward a closing angle 344 in order to move the distal elements 318 and the arms of the tissue gripper 316, as well as any target tissue 370 grasped therebetween, into a closed position. In some embodiments, the closing angle 344 will be 60 degrees, or will range from 0 to 90 degrees (e.g., 0 to 30 degrees or 30 to 60 degrees or 60 degrees to 90 degrees). In other embodiments, closing or partially closing the distal elements is omitted. For example, the tissue gripping system 300 or components thereof may be left in place or may be considered as properly positioned after moving the tissue gripper 316 through the actuation angle 342, without additional closing of the tissue gripping system 300.

Various tissue gripping and/or tissue fixation procedures may call for different closing angles 344 to be used. For example, a closing angle 344 of 60 degrees or less may be useful in assessing the sufficiency of a tissue grasping attempt in a mitral valve regurgitation procedure, and a closing angle 344 that is greater than 60 degrees (e.g., up to 180 degrees) may be useful in a functional mitral valve regurgitation procedure and/or in assessing the sufficiency of a tissue grasping attempt in a functional mitral valve regurgitation procedure.

IV. Methods of Manufacture

Figure 12A:
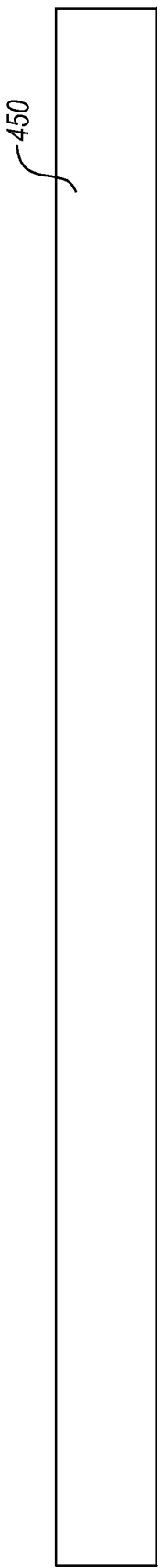
FIGS. 12A-12C illustrate an embodiment of a method of manufacture of a tissue gripping device.
Figure 12B:
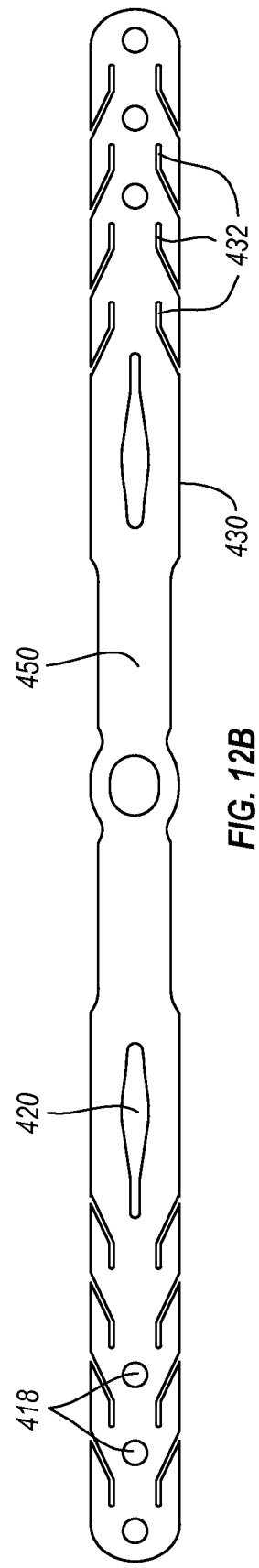
Figure 12C:
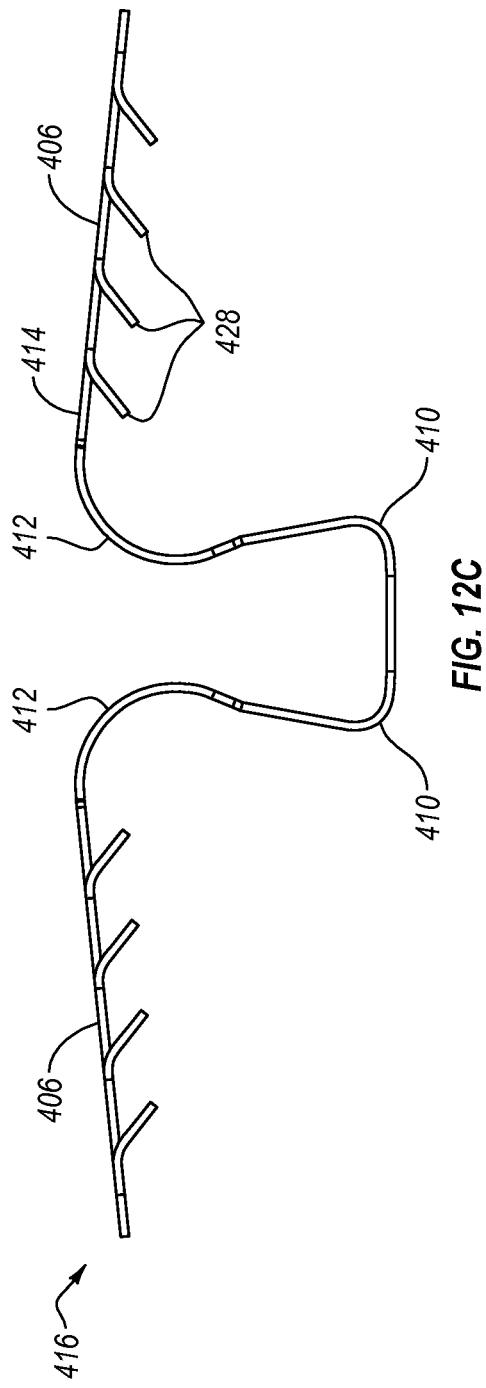

Embodiments of tissue gripping devices of the present disclosure may be manufactured by forming a tissue gripper from a shape-memory material (such as nitinol), as illustrated in FIGS. 12A-12C. Forming the tissue gripper may be accomplished by cutting a pattern shape from a shape-memory stock material 450. The stock material 450 can be strip stock, sheet stock, band stock, or other forms of stock material.

The stock material 450 may be subjected to a subtractive manufacturing processes in order to prepare the stock material 450 with a suitable size and shape prior to further manufacturing. For example, grinding of one or more surfaces of the stock material 450 may be carried out in order to achieve a desired dimension and/or a desired uniformity along a given direction (e.g., grinding of a top and/or bottom surface to achieve a desired thickness).

As illustrated in FIG. 12B, various structural features (e.g., furcated sections 420, holes 418, slotted recesses 432) may be formed in the stock material 450. This may be accomplished using any suitable subtractive manufacturing process such as drilling, lathing, die stamping, cutting, or the like. In preferred embodiments, features are formed using a laser cut or wire-EDM process. For example, in preferred embodiments, a plurality of slotted recesses 432 are formed in the stock material 450 using a laser cutting process. In some embodiments, other features may be added using an additive manufacturing process.

As illustrated in FIG. 12C, in some embodiments, the tissue gripper may be further processed through a shape setting process. For example, one or more bend features may be formed in the tissue gripper by subjecting the tissue gripper to a heated shape setting process in order to set the shape of the bend(s) in the shape-memory material of the tissue gripper. For example, in embodiments including grippers formed from nitinol, the austenite phase (i.e., parent phase or memory phase) can be set with the desired bend features. In some embodiments, this requires positioning and/or forming the desired shape while heating the gripper to a temperature high enough to fix the shape as part of the austenite phase (e.g., 300 to 700 degrees C.).

For example, one or more of the base bend features 410, arm bend features 412, and frictional elements 428 may be formed in a heat shape setting process. In some embodiments, these features may be set at the same time in one heat shape setting process. In other embodiments, multiple heat shape setting steps may be used, such as a first heat shape setting process to form the base bend features 410, followed by a second heat shape setting process to form the arm bend features 412, followed by a third heat shape setting process to form the frictional elements 428 (e.g., by bending portions of the side edge 430 adjacent to slotted recesses 432 in order to form distally and inwardly projecting barbs). In yet other embodiments, other combinations of features may be set in any suitable number of heat shape setting steps in order to form the tissue gripper 416.

In preferred embodiments, the arm bend features 412 are formed in a heat shape setting process such that the angle between the opposing arms 406, as measured from a proximal side 414 while the tissue gripper 416 is in a relaxed configuration, is 180 degrees or is slightly more than 180 degrees (e.g., 185 to 200 degrees). In such embodiments, the tissue gripper 416 formed as a result of the manufacturing process can be moved into a pre-deployed configuration by bending the arm bend features 412 to move the arms 406 proximally and inwardly. In such a stressed state, the arms 406 will resiliently flex toward the relaxed configuration for the full range of angles up to the relaxed configuration of 180 degrees or slightly more than 180 degrees. In addition, because the tissue gripper 416 is formed of a shape-memory material such as nitinol, and is configured to exhibit super-elasticity at operational and physiological temperatures, the arms 406 of the tissue gripper 416 are able to move from the relaxed configuration to the pre-deployed configuration without being plastically deformed, and are thus able to fully flex toward the original relaxed configuration and return to the original relaxed configuration.

In some embodiments, one or more additional manufacturing processes may be performed to prepare a tissue gripper 416. For example, mechanical deburring (e.g., small particulate blasting) and/or electropolishing (e.g., to clean edges and passivate the tissue gripper 416) may be performed on the tissue gripper 416, or on parts thereof. Such additional processes may be done prior to, intermittent with, or after one or more heat shape setting processes. In addition, the tissue gripper 416 may be cleaned in an ultrasonic bath (e.g., with DI water and/or isopropyl alcohol, in combination or in succession).

V. Kits

Kit embodiments can include any of the components described herein, as well as additional components useful for carrying out a tissue gripping procedure. Kits may include, for example, a tissue gripping system as described herein, including a tissue gripper, distal elements, actuator rod, and actuator lines (such as lock lines and gripper lines), a delivery catheter, and a handle, the tissue gripping system being couplable to the delivery catheter at a distal end of the delivery catheter and the handle being couplable to the delivery catheter at a proximal end of the delivery catheter. In such embodiments, the actuator lines and/or actuator rod can pass from the tissue gripping system through lumens of the delivery catheter and to the handle, and the handle can include one or more controls for actuating or otherwise controlling the components of the tissue gripping system.

Some embodiments of kits may include additional interventional tools, such as a guidewire, dilator, needle, and/or instructions for use. Instructions for use can set forth any of the methods described herein. The components of the kit can optionally be packaged together in a pouch or other packaging, and in preferred embodiments will be sterilized. Optionally, separate pouches, bags, trays, or other packaging may be provided within a larger package such that smaller packages can be opened separately to separately maintain the components in a sterile manner.

The terms "approximately," "about," and "substantially" as used herein represent an amount or condition close to the stated amount or condition that still performs a desired function or achieves a desired result. For example, the terms "approximately," "about," and "substantially" may refer to an amount that is within less than 10% of, within less than 1% of, within less than 0.1% of, and within less than 0.01% of a stated amount. In addition, unless expressly described otherwise, all amounts (e.g., temperature amounts, angle measurements, dimensions measurements, etc.) are to be interpreted as being "approximately," "about," and/or "substantially" the stated amount, regardless of whether the terms "approximately," "about," and/or "substantially."

Additionally, elements described in relation to any embodiment depicted and/or described herein may be combinable with elements described in relation to any other embodiment depicted and/or described herein. For example, any element described in relation to an embodiment depicted in FIGS. 9A-9C may be combinable an embodiment described in FIGS. 11A-11C.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

The invention claimed is:

1. A tissue fixation system configured for intravascular delivery, comprising:
    a center portion;
    first and second distal elements moveable relative to the center portion; and
    a gripping device having first and second gripper arms respectively moveable relative to the first and second distal elements, the first and second gripper arms being resiliently biased such that the first and second gripper arms are biased from a stressed state toward a relaxed state,
    wherein the first and second gripper arms define a first angle between them when in the stressed state and a second angle between them when in the relaxed state, the second angle being greater than or equal to 90 degrees, the first angle being less than the second angle.

2. The system of claim 1, wherein the second angle is greater than or equal to 120 degrees.

3. The system of claim 1, wherein the second angle is greater than or equal to 180 degrees.

4. The system of claim 1, wherein the gripping device is made from a memory metal material having an austenite phase corresponding to the relaxed state.

5. The system of claim 1, wherein the gripping device further includes a base section, wherein the first and second gripper arms respectively include first and second arm bend features connecting the first and second gripper arms to the base.

6. The system of claim 5, wherein each of the first and second arm bend features include a furcated section having a first end portion having a first maximum cross-dimension defining a widest location within the first end portion and a second end portion having a second maximum cross-dimension defining a widest location within the second end portion, the first maximum cross-dimension different from the second maximum cross dimension.

7. The system of claim 5, wherein the base includes first and second base bend features, the base being connected to the center portion.

8. The system of claim 1, further comprising a first gripper line coupled to the first gripper arm, wherein tensioning the first gripper line causes the first gripper actuator to be in the stressed state, and relaxing the first gripper line causes the first gripper actuator to move toward the relaxed state under its own bias.

9. The system of claim 8, further comprising a second gripper line coupled to the second gripper line, wherein tensioning the second gripper line causes the second gripper arm to be in the stressed state, and relaxing the second gripper line causes the second gripper arm to move toward the relaxed state under its own bias.

10. A tissue fixation system configured for intravascular delivery, comprising:
    a center portion defining a longitudinal axis;
    a first distal element moveable relative to the longitudinal axis between a pre-deployed configuration and a deployed configuration, the first distal element forming an opening angle relative to the longitudinal axis when in the deployed configuration, the opening angle being greater than or equal to 45 degrees; and
    a gripping device having a first gripper arm being resiliently biased such that the first gripper arm is moveable relative to the first distal element from a stressed state toward a relaxed state, the first gripper arm forming a first angle relative to the longitudinal axis when in the stressed state and a second angle relative to the longitudinal axis when in the relaxed state, the second angle being greater than or equal to the opening angle of the first distal element, and the first angle being less than the second angle.

11. The system of claim 10, wherein the opening angle is 60 degrees.

12. The system of claim 11, wherein the second angle is 60 degrees.

13. The system of claim 11, wherein the second angle is 90 degrees.

14. The system of claim 10, further comprising a second distal element and wherein the gripping device further includes a second gripper arm being resiliently biased such that the second gripper arm is moveable relative to the second distal element from a stressed state toward a relaxed state.

15. The system of claim 14, wherein the first and second gripper arms form a gripper arm angle therebetween when in the relaxed state, the gripper arm angle being greater than or equal to 90 degrees.

16. A tissue fixation system configured for intravascular delivery, comprising:
    a center portion defining a longitudinal axis;
    first and second distal elements moveable relative to the center portion between a pre-deployed configuration and a deployed configuration, the first and second distal elements each defining an opening angle relative to the longitudinal axis when in the deployed configuration, the opening angle being greater than or equal to 45 degrees; and
    a gripping device having first and second distal elements moveable relative to the center portion between a pre-deployed configuration and a deployed configuration, the first and second distal gripping elements each defining an actuation angle relative to the longitudinal axis when in the deployed configuration thereof, the actuation angle being substantially equal to the opening angle.

17. The system of claim 16, wherein the opening angle is 60 degrees.

18. The system of claim 16, wherein the gripping device further includes a base section and the first and second gripper arms respectively include first and second arm bend features connecting the first and second gripper arms to the base section.

19. The system of claim 18, wherein each of the first and second arm bend features include a furcated section having an opening with a terminal distal end formed with a first radius, a terminal proximal end formed with a second radius, and an intermediate portion having a cross-section larger than both the terminal distal and proximal ends, wherein the second radius is smaller than the first radius.

20. The system of claim 16, wherein the first and second gripper arms are resiliently biased such that they each have a stressed state and a relaxed state, the gripper arms being biased toward the relaxed state in which the first and second gripper arms form a relaxed angle therebetween that is greater than the actuation angle.

* * * * *